(12) United States Patent
Chan et al.

(10) Patent No.: US 7,250,120 B2
(45) Date of Patent: Jul. 31, 2007

(54) BENZO-, NAPHTHO- AND PHENANTHROCHROMENE SUBSTITUTED BY CARBAMATED OR UREATED PHENYLS, PREPARATION THEREOF AND COMPOSITIONS AND ARTICLES CONTAINING THEM

(75) Inventors: You-Ping Chan, Lyons (FR); Olivier Breyne, Lyons (FR)

(73) Assignee: Corning Inc., Corning, NY (US)

( * ) Notice: Subject to any disclaimer, the term of this patent is extended or adjusted under 35 U.S.C. 154(b) by 393 days.

(21) Appl. No.: 10/867,201

(22) Filed: Jun. 14, 2004

(65) Prior Publication Data
US 2005/0092972 A1    May 5, 2005

(30) Foreign Application Priority Data
Nov. 5, 2003    (EP) ............... 03 292 764

(51) Int. Cl.
*G02B 5/23*    (2006.01)
*C07D 311/60*    (2006.01)
*C07D 311/78*    (2006.01)
*C07D 311/92*    (2006.01)

(52) U.S. Cl. ............ 252/586; 549/381; 549/382; 549/384; 549/389; 549/406

(58) Field of Classification Search ......... 549/381, 549/382, 384, 389, 406; 252/586
See application file for complete search history.

(56) References Cited

U.S. PATENT DOCUMENTS

| | | | |
|---|---|---|---|
| 3,567,605 A | 3/1971 | Becker | 204/158 |
| 3,627,690 A | 12/1971 | Casella et al. | 252/300 |
| 4,826,977 A | 5/1989 | Heller et al. | 544/70 |
| 5,200,226 A | 4/1993 | Sanchez Rodriguez | 426/585 |
| 5,238,981 A | 8/1993 | Knowles | 524/110 |
| 5,411,679 A | 5/1995 | Kumar | 252/58 |
| 5,451,344 A | 9/1995 | Knowles et al. | 252/586 |
| 5,458,814 A | 10/1995 | Kumar et al. | 252/586 |
| 5,527,911 A | 6/1996 | Guglielmetti | 544/250 |
| 5,645,767 A | 7/1997 | Van Gemert | 252/586 |
| 5,651,923 A | 7/1997 | Kumar et al. | 252/586 |
| 5,698,141 A | 12/1997 | Kumar | 252/586 |
| 5,783,116 A | 7/1998 | Lin | 252/586 |
| 6,329,482 B1 | 12/2001 | Henry | 526/260 |
| 6,506,538 B1 | 1/2003 | Breyen et al. | 430/270 |

FOREIGN PATENT DOCUMENTS

| | | |
|---|---|---|
| FR | 2837200 | 9/2003 |
| JP | 2001-114775 | 4/2001 |
| WO | WO A 9422850 | 10/1994 |
| WO | WO A 95 05382 | 2/1995 |
| WO | WO 95/27716 | 10/1995 |
| WO | WO A 96 14596 | 5/1996 |
| WO | WO A 97 21698 | 6/1997 |
| WO | WO 01/36406 | 5/2001 |

OTHER PUBLICATIONS

J. Org. Chem. 1977, 42, 3403.
Crano, et al., "Spiroxazines and their use in photochromic lenses", published in *Applied Photochromic Polymer Systems* Chapter 2, (Ed. Blackie & Son Ltd., 1992).

Primary Examiner—Bernard Dentz
(74) Attorney, Agent, or Firm—Siwen Chen

(57) ABSTRACT

Disclosed are novel benzo-, naphtho- and phenanthrochromenes substituted by carbamated or ureated phenyls having the following general formula (I):

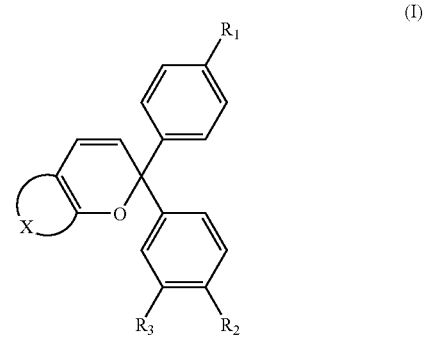

wherein $R_1$ represents a group

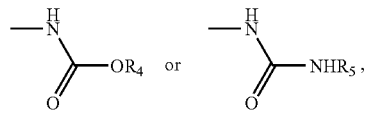

their preparation, photochromic compositions and articles containing them. This family of compounds have interesting and useful photochromic properties, especially in terms of absorption band and discoloration speed.

19 Claims, No Drawings

BENZO-, NAPHTHO- AND PHENANTHROCHROMENE SUBSTITUTED BY CARBAMATED OR UREATED PHENYLS, PREPARATION THEREOF AND COMPOSITIONS AND ARTICLES CONTAINING THEM

FIELD OF THE INVENTION

The present invention relates to benzo-, naphtho- and phenanthropyran type organic compounds having photochromic properties, preparation thereof and photochromic composition, and articles containing them. In particular, the present invention relates to such photochromic compounds substituted by carbamated or ureated phenyls, preparation thereof and photochromic compositions and articles containing them. The present invention is useful, for example, in the manufacture of ophthalmic lenses, optical devices and window panes.

BACKGROUND OF THE INVENTION

Photochromic compounds are those capable of reversible color change under the influence of electromagnetic radiation at certain wavelengths. For example, certain photochromic compounds may exhibit a different color when exposed to ultraviolet (UV) radiation or sunlight, and return to their initial colors when the such exposure ceases. Such returning to the initial color may be effected alternatively by thermal treatment and/or exposure to an electromagnetic radiation at a different wavelength.

Photochromic compounds find application in various fields, for example, for the manufacture of photochromic ophthalmic lenses, contact lenses, solar protection glasses, filters, camera optics or photographic apparatus optics or other optical devices and observation devices, glazing, decorative objects, bill elements or even for information storage by optical inscription (coding). The photochromic compounds, sometimes referred to as photochromic dyes, confer photochromic properties to these manufactured articles.

In the field of photochromic ophthalmic optics, and in particular the spectacle lens market, it is desired that a photochromic lens comprising one or more photochromic compounds has the following traits:

a high transmission in the absence of ultraviolet light;

a low transmission (high colorability) under solar irradiation;

acceptable coloration and discoloration kinetics;

a tint desired by the consumer (preferably grey or brown) with preferably a maintenance of the chosen tint during the coloration and discoloration of the lens;

maintenance of the performance and properties within a temperature range of 0-40° C.; and a significant durability, as they are sophisticated and expensive products.

These characteristics are determined, inter alia, by the active photochromic compounds contained in the lens matrices, which must further be compatible with the matrices material, be it organic polymer or inorganic.

In addition, it is now understood that in order to obtain a desirable color of the photochromic ophthalmic lens, such as brown or grey, the use of a combination of at least two complementary photochromic dyes may be necessitated. Such complementary dyes exhibit different colors, viz., they have distinct maximal absorption wavelength in the visible range between 400-700 nm. This combination further imposes other technical requirements of the photochromic compounds. In particular, the coloration and discoloration kinetics of the (two or more) supplementary photochromic dyes may be advantageously essentially identical. The same applies for their stability over time and also for their compatibility with the plastic or inorganic support material.

Among the numerous photochromic compounds described in the art, benzopyrans and naphthopyrans have been documented, for example, in the following literature: U.S. Pat. Nos. 3,567,605; 3,627,690; 4,826,977; 5,200,226; 5,238,981; 5,411,679; 5,429,744; 5,451,344; 5,458,814; 5,651,923; 5,645,767; 5,698,141; WO-A-95 05382; FR-A-2,718,477; WO-A-96 14596; and WO-A-97 21698. Generally, the photochromic compounds have the following reduced formulae (F1), (F1') and (F1"):

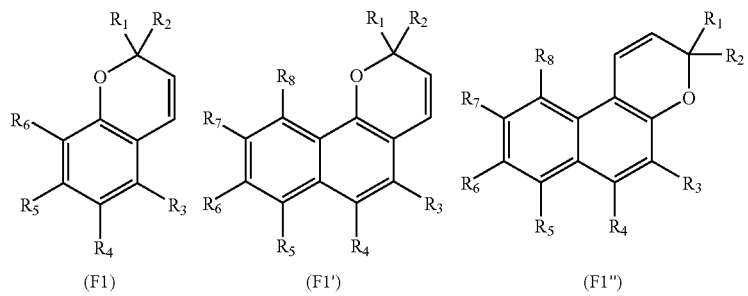

U.S. Pat. No. 5,645,767 describes naphthopyrans (F2) having an indeno group linked to the 5- and 6-carbons of the 2H-naphthopyran skeleton:

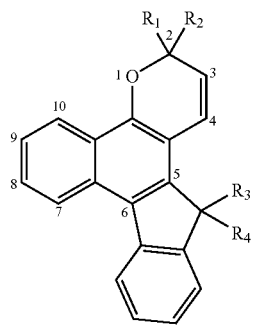

(F2)

U.S. Pat. No. 5,651,923 describes 2H-naphthopyrans (F3, F4) having a naphthofurano or benzo group linked to the 5- and 6-carbons of the 2H-naphthopyran skeleton:

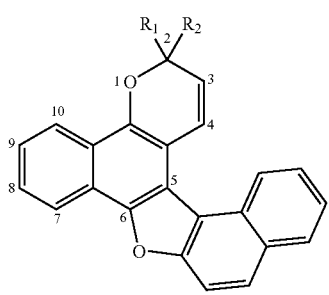

(F3)

(F4)

U.S. Pat. No. 5,783,116 describes derivatives of 2H-naphthopyrans (F5, F6) having a non-substituted alicyclic group:

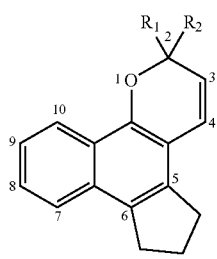

(F5)

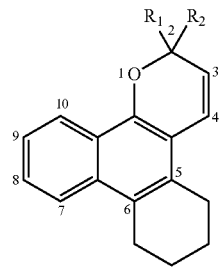

(F6)

WO 01/36406 discloses 3H-naphthopyran derivatives (F7, F8) having a benzo 5- or 6-membered aliphatic ring linked to the 5- and 6-carbon of the 3H-naphthopyran skeleton:

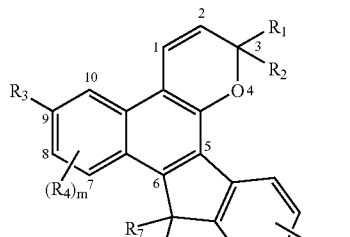

(F7)

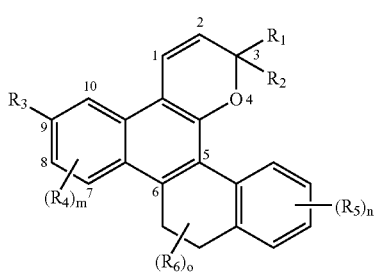

(F8)

U.S. Pat. No. 6,506,538 describes a group of photochromic 2H-naphthopyran compounds having the following general formula (F9) wherein the annelated ring (A) can be (F9-1), (F9-2), (F9-3), (F9-4) and (F9-5):

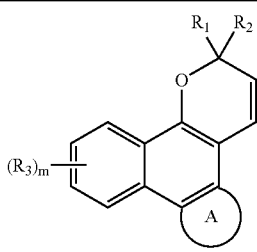

(F9)

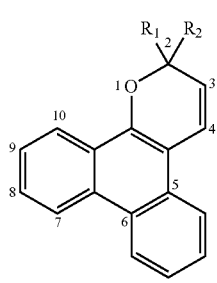

(F9-1)  (F9-2)  (F9-3)  (F9-4)  (F9-5)

These compounds were described in the above references to have photochromic properties. However, in reality, even though these compounds may have one or more of the desired properties described supra, such as a high transmission in the absence of ultraviolet and a high colorability under solar irradiation, few, if any, of the compounds described hitherto have the complete combination of the properties sought after which are necessary for the production of satisfactory articles. In particular, few, if any, of these compounds is intrinsically grey or brown. Therefore, the necessity of using an additional photochromic dye in order to obtain one of these two tints still exists.

In this context, it would be useful to be able to modify the photochromic compounds of each coloration such that final adjustment of the tint is permitted. Taking the formula (F9) supra as an example, where $R_1$ or $R_2$ is a phenyl, the presence of a donor group on the para position can lead to variable amount of bathochromic shift of the absorption band of the photochromic compounds. However, it has been found that the bathochromic shift obtained by substituting an alkoxy group with an amino group is too large (30-40 nm at minimum). Therefore there exists the necessity of obtaining an intermediate shift.

Japanese Patent Application Publication No. 2001-114775 describes compounds where the group $R_1$ is a phenyl substituted on the para position by an amine substituted by electro-attracting groups such as sulphonyls or acetyls. An example compound as disclosed in this document has the following formula (F10):

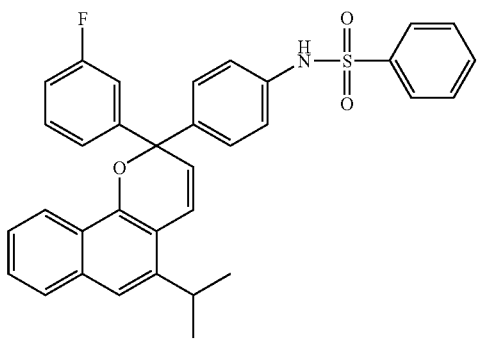

(F10)

The absorption wavelengths were therefore significantly lowered (−15 to −30 nm) relative to the comparative examples having morpholino groups. On the other hand, the discoloration kinetics of the compounds is significantly compromised as discovered by the present inventors, though this was not mentioned in this document.

The inventors of the present invention discovered a group of new compounds having a combination of the desired bathochromic shift in their absorption bands compared with analogous compounds having alkoxy, and, unexpectedly, advantageous photochromic properties, notably more rapid discoloration than those having sulphonyls or acetyls.

DESCRIPTION OF THE INVENTION

According to a first aspect of the present invention, it is provided a compound having the following formula (I)

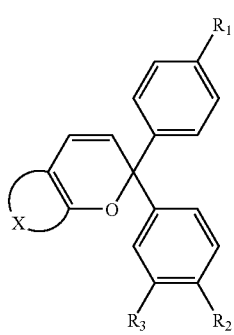

(I)

wherein:
(1) $R_1$ represents a group

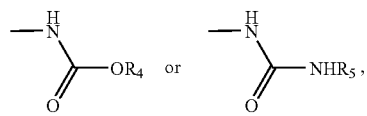

wherein $R_4$ and $R_5$ represent linear or branched alkyl group having 1 to 12 carbon atoms, a benzyl, naphthyl or phenyl group optionally substituted by at least one linear or branched alkyl group having 1 to 6 carbon atoms;
(2) $R_2$ and $R_3$ are defined as follows:
(A) $R_2$ represents one of the following groups:
(A1) a hydrogen;
(A2) a linear or branched alkyl group having 1 to 12 carbon atoms, advantageously 1 to 6 carbon atoms;
(A3) a cycloalkyl group having 3 to 12 carbon atoms;
(A4) a phenyl or benzyl group, optionally substituted;
(A5) a linear or branched alkoxy group having 1 to 12 carbon atoms, advantageously 1 to 6 carbon atoms; and
(A6) a group

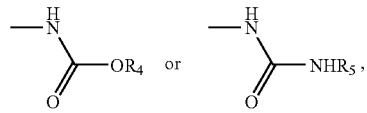

wherein $R_4$ and $R_5$ have the same meaning as defined supra for $R_1$;
(B) $R_3$ represents one of the following groups:
(B1) a hydrogen;
(B2) a linear or branched alkyl group having 1 to 12 carbon atoms, advantageously 1 to 6 carbon atoms;
(B3) a cycloalkyl group having 3 to 12 carbon atoms;
(B4) a phenyl or benzyl group, optionally substituted; and
(B5) a linear or branched alkoxy group having 1 to 12 carbon atoms, advantageously 1 to 6 carbon atoms;
or
(C) the $R_2$ and $R_3$ groups, taken together, form an aromatic or non-aromatic cyclic group having one ring or two annelated rings which can comprise at least one heteroatom selected from the group consisting of: oxygen, sulfur and nitrogen; the aromatic or non-aromatic rings being independently 5 to 7-membered; and
(3) the group

is a benzo, naphtho or phenanthro group optionally substituted or annelated with other aromatic or non-aromatic rings.

Preferably, $R_3$ in formula (I) is hydrogen.

One skilled in the art readily understands that the branched alkyl and alkoxy groups as defined herein should comprise sufficient number of carbon atoms in order that they can be branched.

One skilled in the art also should understand that, from the above description, the compound of the present invention can be benzo-, 2H-naphtho-, 3H-naphtho- or phenanthropyran type compounds. The nature of the group

is not critical for the present invention except for one point: the group must not comprise groups that prevent the opening of the pyran ring which imparts the photochromic properties to the compounds.

For those compounds of formula (I) wherein $R_2$ or $R_3$, $R_4$ and $R_5$ are substituted phenyl or benzyl groups, non-limiting examples of such substituents to these groups include, inter alia, linear or branched alkyl or alkoxy groups comprising 1-6 carbon atoms and halogen, particularly chlorine, fluorine and bromine.

Thus, preferably, the compound of the present invention has one of the following general formulae ($I_a$), ($I_b$), ($I_c$) and ($I_d$):

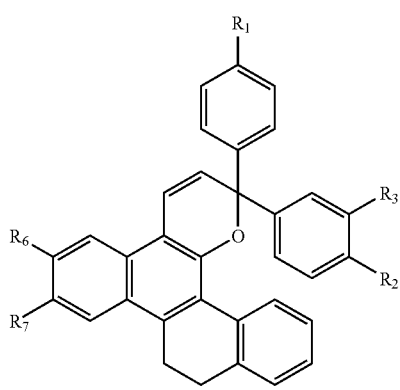

(I$_a$)

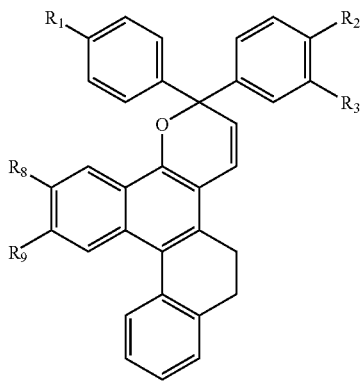

(I$_b$)

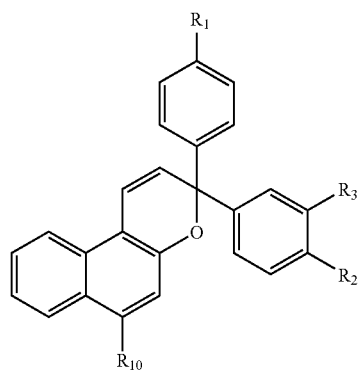

(I$_c$)

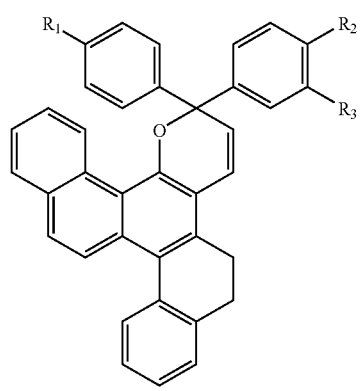

(I$_d$)

wherein
(a) $R_1$, $R_2$ and $R_3$ have the same definition as given supra in relation to formula (I);
(b) $R_6$ represents:
 (b1) a hydroxy;
 (b2) a linear or branched alkyl comprising 1 to 6 carbon atoms;
 (b3) a linear or branched alkoxy group comprising 1 to 6 carbon atoms;
 (b4) a

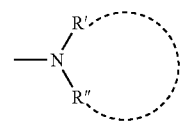

group, where R' and R", identical or different, independently represent a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R'" group, which is a linear or branched alkyl group comprising 1 to 6 carbon atoms;

(c) $R_7$ represents:
(c1) a halogen, and notably fluorine, chlorine or bromine;
(c2) a hydroxy;
(c3) a linear or branched alkyl group comprising 1 to 12 carbon atoms (advantageously 1 to 6 carbon atoms);
(c4) a cycloalkyl having 1-12 carbon atoms;
(c5) a linear or branched alkoxy group comprising 1 to 12 carbon atoms (advantageously 1 to 6 carbon atoms),
(c6) a haloalkyl, halocycloalkyl, or haloalkoxy group corresponding to the alkyl, cycloalkyl, alkoxy groups of (c3), (c4) and (c5) above, respectively, which are substituted with at least one halogen atom, notably selected from fluorine, chlorine and bromine;
(c7) an aryl or heteroaryl group comprising in its basic structure 6 to 24 carbon atoms or 4 to 24 carbon atoms, or 4 to 24 carbon atoms and at least one heteroatom selected from sulfur, oxygen and nitrogen; said basic structure being optionally substituted with at least one substituent selected from the list given below:
   (c7.1) a halogen, and notably fluorine, chlorine and bromine;
   (c7.2) a hydroxy;
   (c7.3) a linear or branched alkyl group comprising 1 to 12 carbon atoms, advantageously 1-6 carbon atoms;
   (c7.4) a linear or branched alkoxy group comprising 1 to 12 carbon atoms, advantageously 1-6 carbon atoms;
   (c7.5) a cycloalkyl group comprising 3 to 12 carbon atoms,
   (c7.6) a haloalkyl, haloalkoxy or halocycloalkyl group corresponding respectively to the alkyl, alkoxy and cycloalkyl defined in (c7.3), (c7.4) and (c7.5), supra, which are substituted with at least one halogen atom, and notably a fluorine atom;
   (c7.7) a phenoxy or naphthoxy group optionally substituted with at least one linear or branched alkyl or alkoxy group comprising 1 to 12 carbon atoms;
   (c7.8) a linear or branched alkenyl group comprising 2 to 12 carbon atoms, and notably a vinyl group or an allyl group;
   (c7.9) an —$NH_2$ group;
   (c7.10) an —NHR group, with R representing a linear or branched alkyl group comprising 1 to 6 carbon atoms, or a phenyl group optionally substituted with at least one linear or branched alkyl group comprising 1 to 6 carbon atoms;
   (c7.11) a

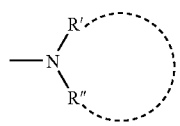

group, where R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R'" group, which is a linear or branched alkyl group comprising 1 to 6 carbon atoms;
   (c7.12) a methacryloyl group or an acryloyl group;
(c8) an aralkyl or heteroaralkyl group, wherein the alkyl group, which is linear or branched, comprises 1 to 4 carbon atoms, and the aryl and heteroaryl groups have the same definition as those given supra in (c7);
(c9) a phenoxy or naphthoxy group optionally substituted with at least one linear or branched alkyl or alkoxy group comprising 1 to 12 carbon atoms,
(c10) an amine, amide, carbamate or urea group: —$NH_2$, —NHR, —NHCOR, —NR'COR, —NHCOOR, —NHCONHR, —$CONH_2$, —CONHR,

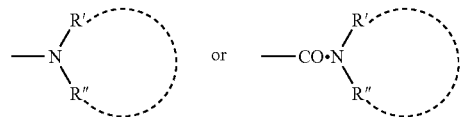

wherein
R represents a linear or branched alkyl group comprising 1 to 6 carbon atoms, or a phenyl group optionally substituted with at least one linear or branched alkyl group comprising 1 to 6 carbon atoms; and R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R'" group, which is a linear or branched alkyl group comprising 1 to 6 carbon atoms;
(c11) an —$OCOR_{11}$ or —$OCOOR_{11}$ group, $R_{11}$ representing a linear or branched alkyl group comprising 1 to 6 carbon atoms, or a cycloalkyl group comprising 3 to 6 atoms, or a phenyl group, optionally substituted with at least one of the substituents listed above in (c7.1) to (c7.12) for the aryl and heteroaryl groups defined in (c7);
or
$R_6$ and $R_7$, taken together, form an aromatic or non-aromatic cyclic group having one ring or two annelated rings, which can comprise at least one heteroatom selected from the group consisting of: oxygen, sulfur and nitrogen;
wherein the aromatic or non-aromatic rings are independently 5 to 7-membered and optionally comprises at least one substituent $R_3$ as defined supra in relation to formula (I);

(d) $R_8$ and $R_9$, identical or different, independently represent:
  (d1) a halogen, and notably fluorine, chlorine or bromine;
  (d2) a hydroxy;
  (d3) a linear or branched alkyl group comprising 1 to 12 carbon atoms (advantageously 1 to 6 carbon atoms);
  (d4) a cycloalkyl group comprising 1-12 carbon atoms;
  (d5) a linear or branched alkoxy group comprising 1 to 12 carbon atoms (advantageously 1 to 6 carbon atoms),
  (d6) a haloalkyl, halocycloalkyl, or haloalkoxy group corresponding to the alkyl, cycloalkyl, alkoxy groups in (d3), (d4) and (d5), respectively, which are substituted with at least one halogen atom, notably selected from fluorine, chlorine and bromine,
  (d7) an aryl or heteroaryl group having the same definition as given above for $R_7$ in (c7) supra;
  (d8) an aralkyl or heteroaralkyl group, wherein the alkyl group, linear or branched, comprises 1 to 4 carbon atoms, and the aryl and heteroaryl groups have the same definition as those given supra in (c7);
  (d9) a phenoxy or naphthoxy group optionally substituted with at least one linear or branched alkyl or alkoxy group comprising 1 to 12 carbon atoms,
  (d10) an amine, amide, carbamate or urea group: —NH₂, —NHR, —NHCOR, —NR'COR, —NHCOOR, —NHCONHR, —CONH₂, —CONHR,

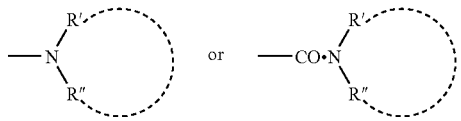

wherein
  R represents a linear or branched alkyl group comprising 1 to 6 carbon atoms, or a phenyl group optionally substituted with at least one linear or branched alkyl group comprising 1 to 6 carbon atoms;
  R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms;
  (d11) an —OCOR₁₁ or —OCOOR₁₁ group, R₁₁ representing a linear or branched alkyl group comprising 1 to 6 carbon atoms, or a cycloalkyl group comprising 3 to 6 atoms, or a phenyl group, optionally substituted with at least one of the substituents listed above from (c7.1) to (c7.12) for the aryl and heteroaryl groups defined in (c7) supra;
or
  $R_8$ and $R_9$, taken together, form an aromatic or non-aromatic cyclic group having one or two annelated rings which can comprise at least one heteroatom selected from the group consisting of oxygen, sulfur and nitrogen; wherein said rings, being 5-7 membered, optionally comprises at least one substituent selected from those listed from (c7.1) to (c7. 12) for the aryl and heteroaryl groups defined in (c7) supra;
(e) $R_{10}$ represents a

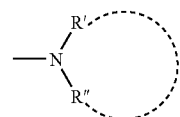

group, where R' and R", identical or different, independently represent a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms.

Among the many formula (I) compounds of the present invention, the following compounds (I1)-(I6) are particularly preferred:

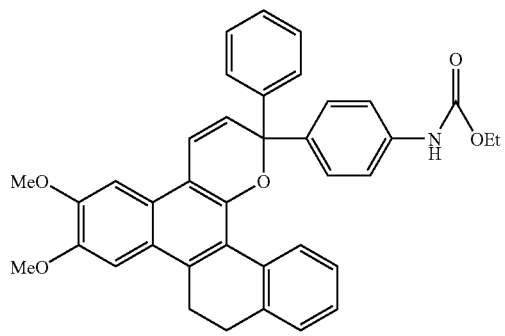

(I1)

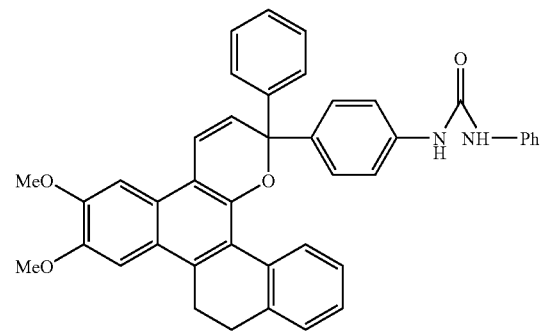

(I2)

-continued

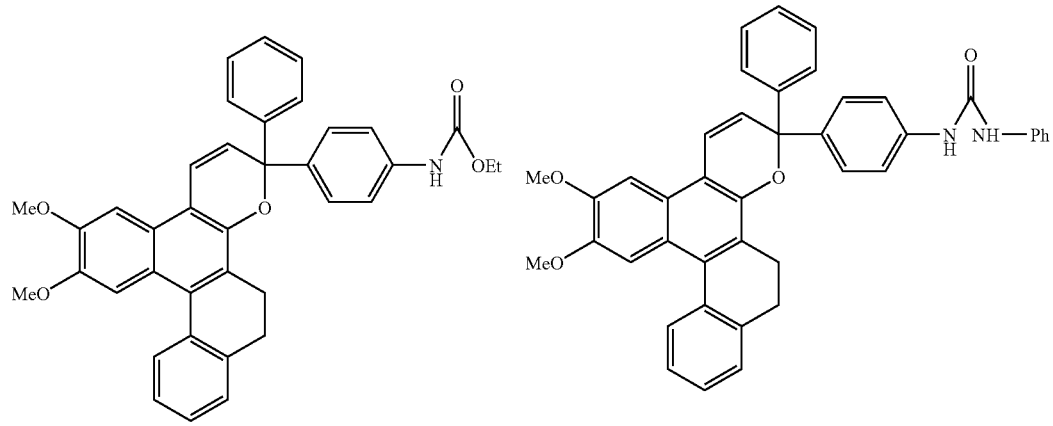

(I3)　　(I4)

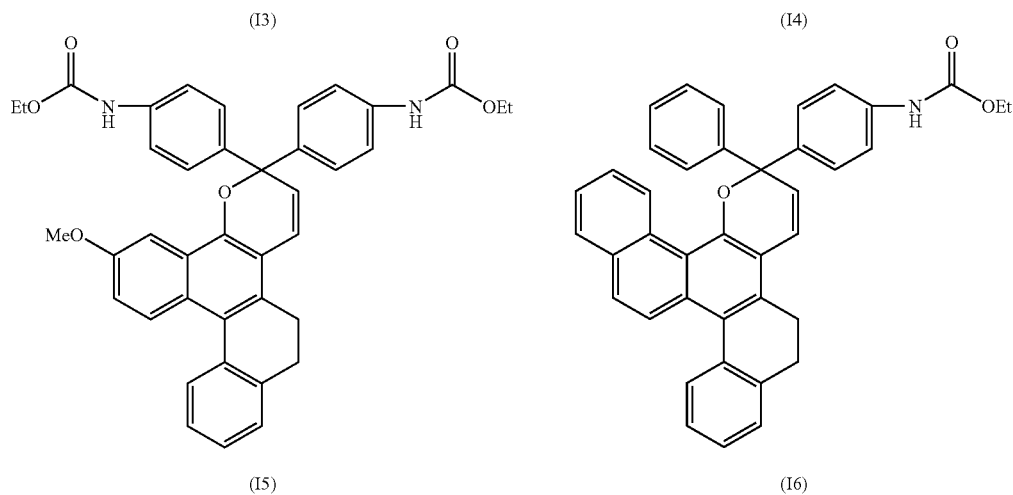

(I5)　　(I6)

Among these compounds, compound (I6) is most preferred.

U.S. Pat No. 6,506,538 does not disclose that in the (F9) formula, where $R_1$ or $R_2$ is an aryl group, it can be substituted by a carbamate or a urea group. In connection with 2H- or 3H-naphthopyrans, none of the documents listed supra discloses a compound where one of the two substituents on the 2- or 3-carbon adjacent to the oxygen on the pyran ring is a phenyl substituted by a carbamate or a urea group.

According to a second aspect of the present invention, it is provided a process or preparing the formula (I) compound as defined supra, characterized in that it comprises either:

(1) the condensation reaction between:
  (i) an intermediate compound having the following formula (II):

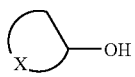

(II)

wherein the group

has the same meaning as defined supra in relation to formula (I); and (ii) a derivative of propargylic alcohol corresponding to the following formula (III):

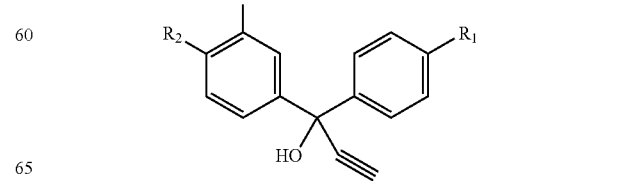

(III)

wherein $R_1$, $R_2$ and $R_3$ have the same meaning as defined supra in relation to formula (I);

wherein the condensation between (II) and (III) is advantageously effected in the presence of a catalyst, the catalyst being preferably selected from the group consisting of p-toluenesulfonic acid, dodecylsulfonic acid, camphorsulfonic acid or bromoacetic acid;
or (2) the condensation reaction between:
the formula (II) compound as defined in (i) supra in this claim, and
(iii) an aldehyde derivative corresponding to the following formula (III'):

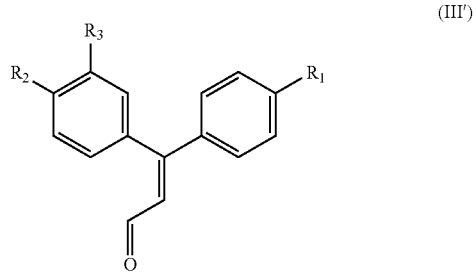

(III')

wherein $R_1$, $R_2$ and $R_3$ have the same meaning as defined supra in relation to formula (I);

wherein the condensation reaction between (II) and (III') is advantageously effected in the presence of a metal complex, preferably a titanium complex, with titanium tetraethylate being particularly preferred.

The condensation reaction between compounds (II) and (III) or (III') can be effected in a solvent such as toluene, xylene or tetrahydrofuran, optionally in the presence of additional catalysts. For a more detailed description of the condensation between compounds (II) and (III'), one can refer to European Patent Application No. EP-A-0 562 915.

Compounds (III) are known to one skilled in the art and can be obtained from the corresponding ketones according to a method particularly described in WO-A-96 14596. The ketones are commercially available or can be prepared according to a method known as the Fredel-Craft reactions (see WO-A-96 14596 and references cited in this document).

The aldehydes (III'), a derivative of compound (III), can be obtained from rearrangement in acid media (see *J. Org. Chem.* 1977, 42, 3403).

The compounds of formula (II) are the phenols, naphthols or phenanthols optionally substituted, the synthesis of which was described in the prior art.

According to a third aspect, the present invention provides a photochromic composition comprising in part at least one photochromic compound of the present invention. The photochromic composition may comprise one of the following:

(1) a compound of the present invention, described supra;
(2) a mixture of at least two compounds of the present invention, described supra;
(3) a mixture of at least one compound of the present invention, described supra, and at least one other type of photochromic compound and/or at least one non-photochromic colorant; and
(4) a linear or reticulated (co)polymer obtained by polymerization and/or reticulation and/or grafting of at least one compound of the present invention, described supra.

For example, on the one hand, the photochromic composition of the present invention may constitute the chromenes having formula (I) as described supra, used separately or in combination with other chromenes of the present invention and/or with at least one other type of photochromic compound and/or with at least one non-photochromic colorant.

For example, on the other hand, the photochromic composition of the. present invention can comprise the compound (I) of the present invention as defied supra, and/or at least one linear or reticulated (co)polymer containing in the structure at least one compound (I) of the present invention. This photochromic composition may comprise other type of photochromic compounds and/or at least one non-photochromic colorant and/or at least one stabilizer. One skilled in the art can choose the photochromic compounds of another type, non-photochromic colorants and stabilizers to obtain desired properties of the composition once the photochromic compound of the present invention and the polymer are chosen.

Within the context of the present invention, combinations of photochromic compounds of the present invention and/or combinations of photochromic compounds of the present invention and photochromic compounds of another type according to the prior art are particularly recommended. Such combinations are interesting in that they may be suitable for generating grey or brown tints, which are particularly desired by consumers of applications such as ophthalmic spectacles or solar spectacles. Those complementary photochromic compounds can be those known to one skilled in the art and described in the prior art, for example, chromenes (U.S. Pat. Nos. 3,567,605; 5,238,981; WO-A-9422850; EP-A-0 562 915), spiropyrans or naphthopyrans (U.S. Pat. No. 5,238,981) and spiroxazines (Crano et al., "*Applied Photochromic Polymer Systems,*" Chapter 2, (Ed. Blackie & Son Ltd., 1992)).

The photochromic composition according to the present invention can also comprise at least one of the following:
non-photochromic compounds for the adjustment of tint;
one or more stabilizers, for example, antioxidants;
one or more anti-UV agents;
one or more free radical scavengers; and
one or more photochromic excited state deactivators.

These additives can notably improve the durability of the photochromic compositions.

The compounds and the photochromic compositions envisaged in the context of their photochromic applications can be used in solution. Thus, a photochromic solution can be obtained by dissolving at least one of the said compounds or compositions in an organic solvent such as toluene, dichloromethane, tetrahydrofuran or ethanol. The solutions obtained are in general colorless and transparent. When exposed to sunlight, they develop a strong coloration and regain the colorless state when they are placed in an area of less exposure to the solar radiation or, in other words, when they are no longer subject to UV radiation. In general, a very low concentration of product (on the order of 0.01 to 5% by weight) is sufficient to obtain an intense coloration.

The compounds and photochromic compositions of the present invention are furthermore compatible with supporting matrices of organic polymer or of inorganic material, in a form included in said matrices as well as in the form of a coating on said matrices. These matrices may constitute part of the photochromic composition of the present invention.

The most interesting applications of the compounds of the invention are in fact those photochromic compositions of the present invention in which the photochromic agents are dispersed within, near or on the surface of a matrix formed by a polymer, and/or copolymer and/or mixture of (co) polymers. In these photochromic compositions, the photochromic agents, including the compounds of the present invention, may be dispersed uniformly within the matrix, or distributed only in part of the matrix, such as the part near the surface uniformly or unevenly.

Similar to their behavior in solutions, the compounds (I) of the present invention included in a polymer matrix are colorless or slightly colored in the initial un-darkened state and rapidly develop an intense coloration under UV radiation (365 nm) or under a light source similar to the solar radiation. They return to the initial coloration after the irradiation ceases to exit.

The method of implementation envisaged to obtain such a matrix varies widely. Amongst those known to one skilled in the art, the diffusion in the (co)polymer, from a suspension or solution of the photochromic compound, in a silicone oil, in an aliphatic or aromatic hydrocarbon, or in a glycol, or from another polymer matrix, can be cited as examples. The diffusion is commonly carried out at a temperature of 50 to 200° C. for a period of time of 15 minutes to several hours, according to the nature of the polymer matrix. Another implementation technique consists in mixing the photochromic compounds in a formulation of polymerizable mixture, depositing this mixture on a surface or in a mould, and then carrying out the copolymerization to form the matrix. These implementation techniques, and others, are described in the article by Crano et al., "*Spiroxazines and their use in photochromic lenses*", published in *Applied Photochromic Polymer Systems* (Ed. Blackie and Son Ltd., 1992).

Polymers comprised of or selected from the following may be mentioned as examples of preferred polymer materials for forming matrices and/or the photochromic composition of the present invention which are useful in optical applications of the photochromic compounds according to the present invention:

(1) Alkyl, cycloalkyl, (poly or oligo)ethylene glycol, aryl or arylalkyl mono-, di-, or tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group;

(2) Polystyrene, polyether, polyester, polycarbonate (e.g., bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinyllic polymers, cellulose acetate, cellulose triacetate, cellulose acetate-propionate or polyvinylbutyral;

(3) difunctional monomers having the formula (Z) below:

wherein (i) $R_{10}$, $R'_{10}$, $R_{11}$ and $R'_{11}$, identical or different, independently represent a hydrogen or a methyl group;

(ii) m and n are independently integers between 0 and 4 inclusive, and are advantageously independently equal to 1 or 2;

(iii) X and X', identical or different, are a halogen and preferably represent a chlorine and/or a bromine; and (iv) p and q are, independently, integers between 0 and 4 inclusive; and (4) copolymers of at least two types of copolymerizable monomers defined supra from (1) to (3), and preferably those of (meth)acrylic, vinylic, allylic types and their mixtures.

In a particularly preferred manner, the photochromic compounds of the present invention are used with resins which have a nanobiphasic structure and which are obtained by copolymerizing at least two different, specific difunctional monomers. Such resins have been described in the French Patent Publication No. FR-A-2 762 845.

The amount of the photochromic compounds in the (co) polymer matrix depends upon the properties of the compounds and matrix, and, the degree of darkening desired. Usually, between 0.001 and 20% by weight of it is used.

As indicated supra, the photochromic agents may be dispersed uniformly within the body of the polymeric matrix, or may be distributed only in part of the matrix, such as in the near-surface parts. Or alternatively, the photochromic composition of the present invention may form a surface coating on the polymer matrix. Preferably, the photochromic agents, including the compounds of the present invention, are distributed uniformly within the polymer matrix.

Still another aspect of the present invention in relation to the formula (I) photochromic compounds is optical articles, such as ophthalmic or solar spectacles, comprising the photochromic compositions of the present invention, described supra. For example, the optical articles may comprise:

at least one compound (I) according to the present invention; and/or at least one (co)polymer and/or reticulate formed, at least in part, from compound(s) of the present invention; and/or at least one matrix, as described supra, or an organic polymer material or of an inorganic material, or even of a hybrid inorganic-organic material, said matrix initially optionally comprising at least one compound of the present invention.

In practice, the articles which are more particularly covered by the present invention are ophthalmic lenses or photochromic solar lenses, window panes (such as those for

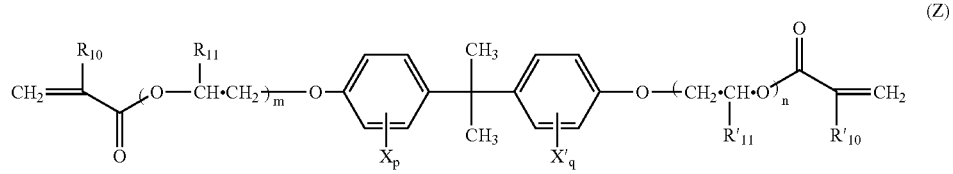

buildings, locomotion engines and automobile vehicles), optical devices, decorative articles, solar protection articles, information storage, etc.

The following non-limiting examples further illustrate the present invention. Compounds (1)-(6) of the present invention and comparative compounds (C1)-(C6) were synthesized, studied and compared in these examples.

EXAMPLES

Example 1

Synthesis of Compound (1)

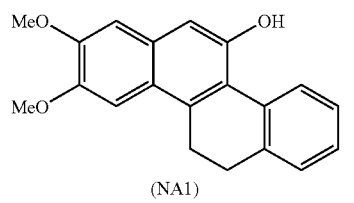
(NA1)

+

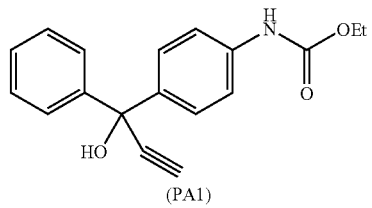
(PA1)

→

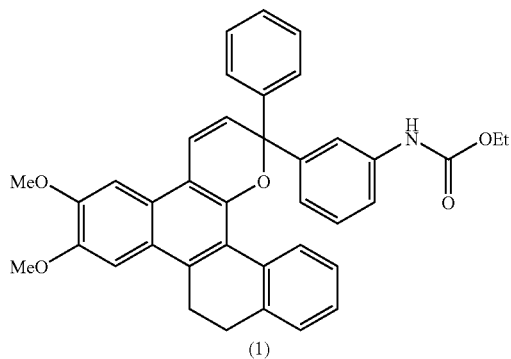
(1)

The preparation of naphthol (NA1) was disclosed in the prior art, such as WO-A-01-36406.

To a solution of 613 mg naphthol (NA1) and 738 mg propargylic alcohol (PA1) in 10 ml toluene was added 23 mg of camphorsulfonic acid. The reaction mixture was stirred at 55° C. for 2 hours, then purified by filtration over silica gel. The solid obtained was recrystalized to produce 638 mg pure crystal. ¹H NMR of the crystal indicated it was pure compound (1).

Example 2

Synthesis of Compound (2)

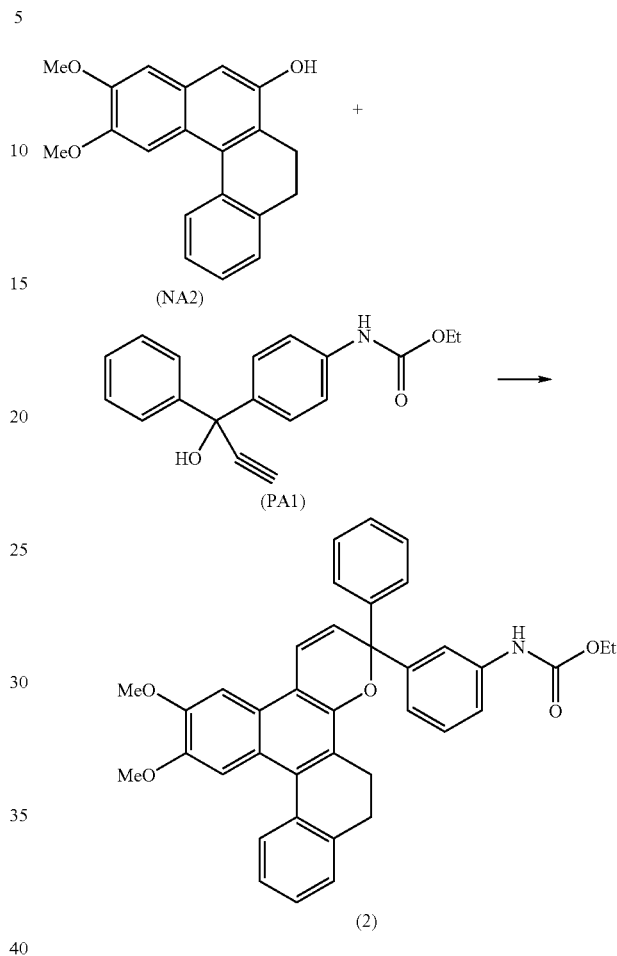

To a solution of 429 mg naphthol (NA2) and 528 mg propargylic alcohol (PA1) in 10 ml toluene was added 23 mg of camphorsulfonic acid. The reaction mixture was stirred at 55° C. for 2 hours, then purified by filtration over silica gel. The solid obtained was recrystalized to produce 150 mg pure crystal. ¹H NMR of the crystal indicated it was pure compound (2).

Example 3

Synthesis of Compound (3)

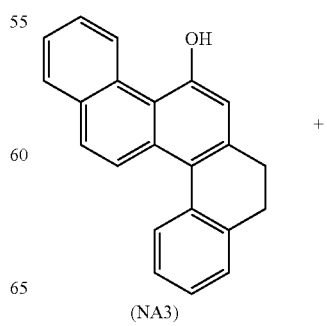
(NA3)

+

-continued (PA1)

(3)

To a solution of 5.9 g phenanthol (NA3) and 6.4 g propargylic alcohol (PA1) in 40 ml toluene was added 229 mg camphorsulfonic acid. The reaction mixture was stirred for 3.5 hours at 60° C., then purified by filtration over silica gel. The solid obtained was recrystalized to produce 9.7 g pure crystal. $^1$H NMR characterization indicated it was pure compound (3).

Example 4

Synthesis of Compound (4)

(NA4)

(PA2)

-continued (4)

To a solution of 590 mg naphthol (NA4) and 900 mg propargylic alcohol (PA2) in 10 ml toluene was added 300 mg camphorsulphonic acid. The reaction mixture was stirred for 2 hours at 60° C., then purified by filtration over silica gel. The solid obtained was recrystalized to produce 90 mg pure crystal. $^1$H NMR characterization indicated it was pure compound (4).

Example 5

Synthesis of Compound (5)

(NA1)

(PA3)

(5)

To a solution of 500 mg naphthol (NA1) and 1170 mg propargylic alcohol (PA3) in 10 ml toluene was added 40 mg of camphorsulfonic acid. The reaction mixture was stirred at 60° C. for 2 hours, then purified by filtration over silica gel. The solid obtained was recrystalized to produce 90 mg pure crystal. ¹H NMR of the crystal indicated it was pure compound (5).

Example 6

Synthesis of Compound (6)

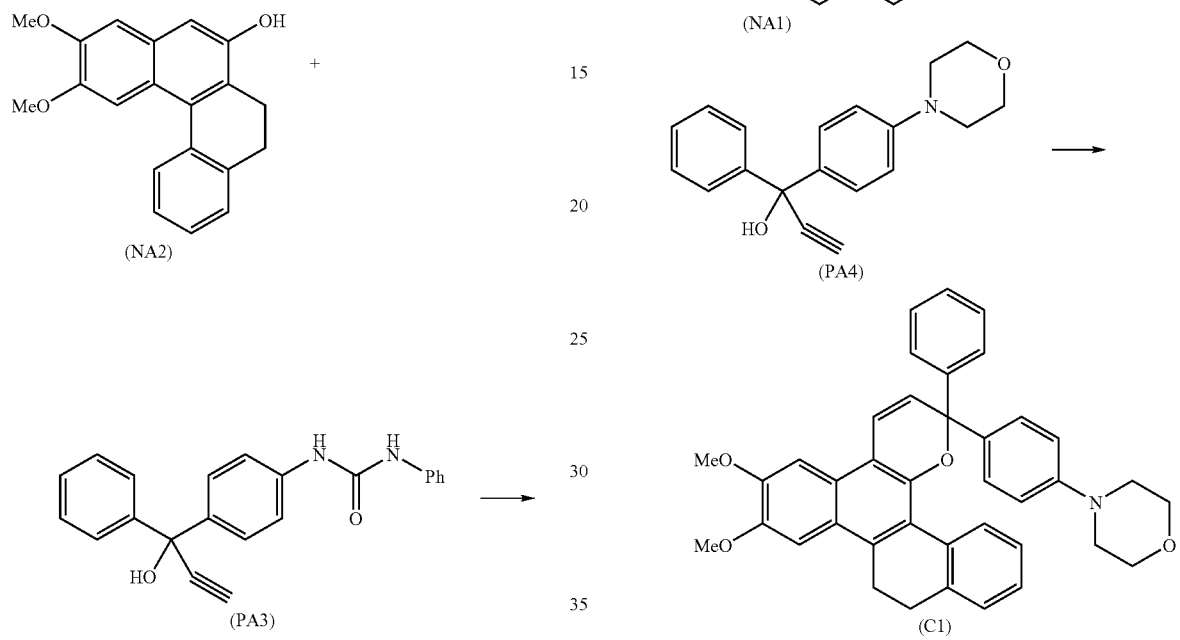

Example 7 (Comparative Example)

Synthesis of Compound (C1)

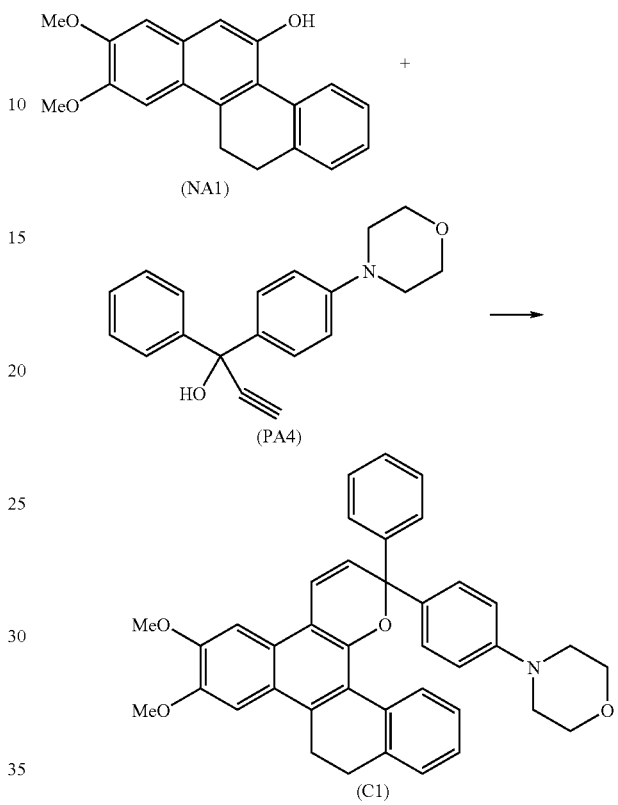

To a solution of 613 mg naphthol (NA1) and 645 mg propargylic alcohol (PA4) in 10 ml toluene is added 23 mg camphorsulfonic acid. The reaction mixture was stirred at 65° C. for 1.5 hours, then purified by filtration over silica gel. The solid obtained was recrystalized to produce 750 mg pure crystal. ¹H NMR characterization indicated that it was pure compound (C1).

Example 8 (Comparative Example)

Synthesis of Compound (C2)

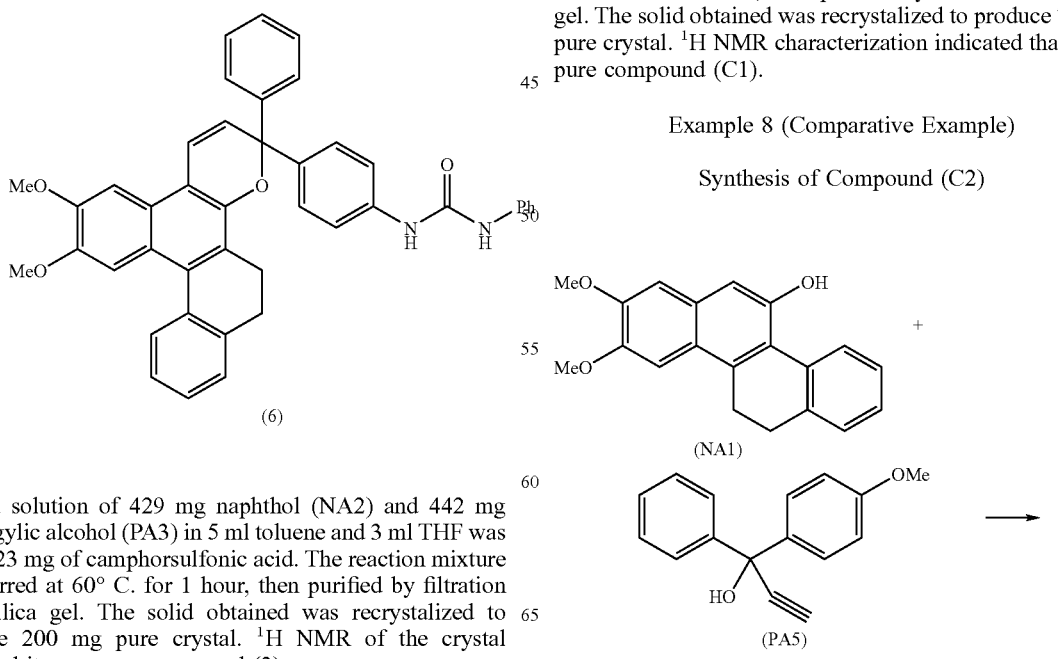

To a solution of 429 mg naphthol (NA2) and 442 mg propargylic alcohol (PA3) in 5 ml toluene and 3 ml THF was added 23 mg of camphorsulfonic acid. The reaction mixture was stirred at 60° C. for 1 hour, then purified by filtration over silica gel. The solid obtained was recrystalized to produce 200 mg pure crystal. ¹H NMR of the crystal indicated it was pure compound (2).

-continued

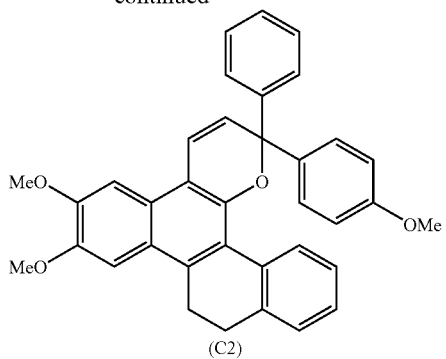

(C2)

To a solution of 507 mg naphthol (NA1) and 516 mg propargylic alcohol (PA5) in 50 ml chloroform was added 20 mg p-toluenesulfonic acid. The reaction mixture was stirred under reflux for 1.5 hours, then purified by filtration over silica gel. The solid obtained was recrystalized to produce 219 mg pure crystal. $^1$H NMR characterization indicated that it was pure compound (C2).

Example 9 (Comparative Example)

Synthesis of Compound (C3)

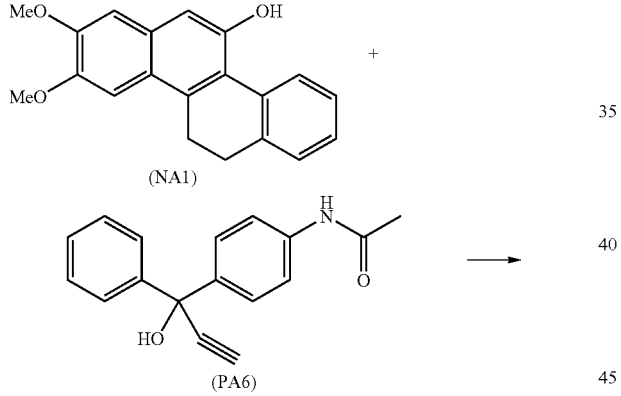

(NA1)

(PA6)

(C3)

To a solution of 500 mg naphthol (NA1) and 900 mg propargylic alcohol (PA6) in 10 ml toluene was added 180 mg camphorsulphonic acid. The reaction mixture was stirred at 65° C. for 1.5 hours, then purified by filtration over silica gel. The solid obtained was recrystalized to produce 60 mg pure crystal. $^1$H NMR characterization indicated that it was pure compound (C3).

Example 10 (Comparative Example)

Synthesis of Compound (C4)

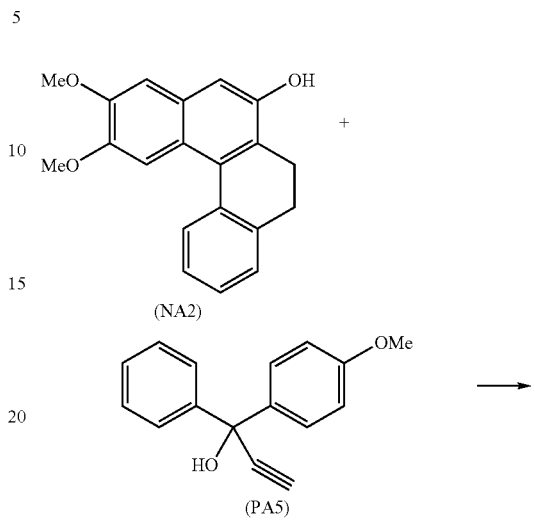

(NA2)

(PA5)

(C4)

To a solution of 600 mg naphthol (NA2) and 476 mg propargylic alcohol (PA5) in 10 ml toluene was added 46 mg camphorsulphonic acid. The reaction mixture was stirred at 50° C. for 2 hours, then purified by silica column chromatography. The solid obtained was recrystalized to produce 330 mg white powder. $^1$H NMR characterization indicated that it was compound (C4).

Example 11 (Comparative Example)

Synthesis of Compound (C5)

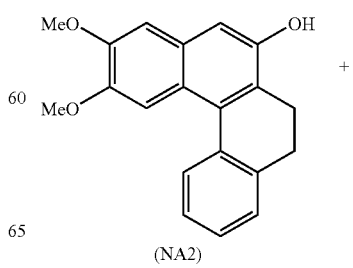

(NA2)

-continued

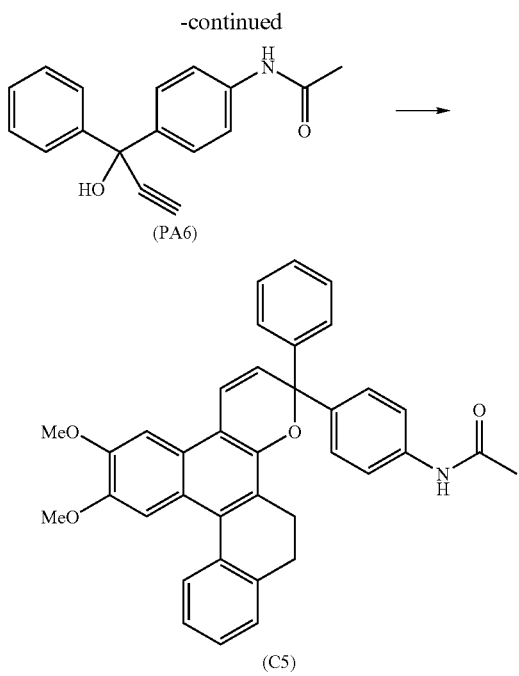

(PA6)

(C5)

To a solution of 400 mg naphthol (NA2) and 620 mg propargylic alcohol (PA6) in 10 ml toluene was added 20 mg camphorsulphonic acid. The reaction mixture was stirred at 60° C. for 2 hours, then purified by filtration over silica gel. The solid obtained was recrystalized to produce 193 mg pure crystal. $^1$H NMR characterization indicated that it was pure compound (C5).

Example 12 (Comparative Example)

Synthesis of Compound (C6)

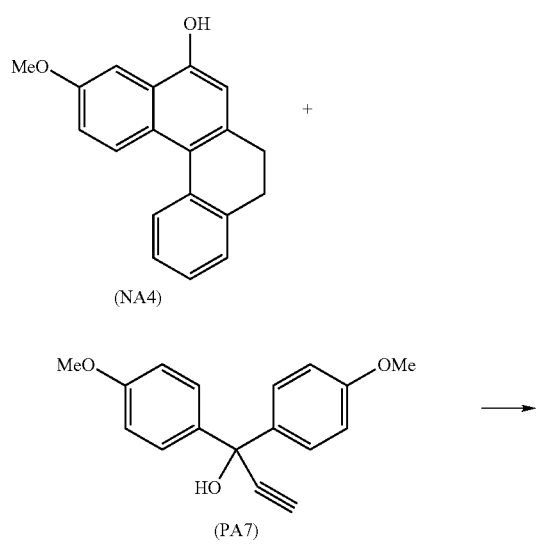

(NA4)

(PA7)

-continued

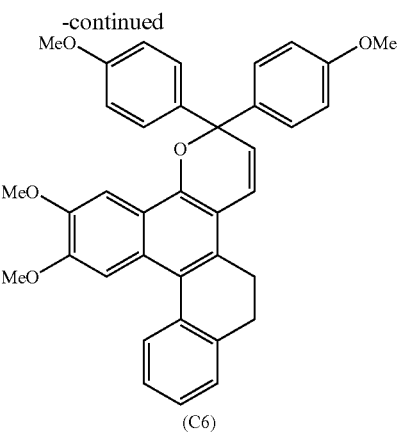

(C6)

To a solution of 553 mg naphthol (NA4) and 500 mg propargylic alcohol (PA7) in 10 ml toluene was added 25 mg camphorsulphonic acid. The reaction mixture was stirred at 60° C. for 2 hours, then purified by filtration over silica gel. The solid obtained was recrystalized to produce 640 mg pure crystal. $^1$H NMR characterization indicated that it was pure compound (C6).

The photochromic properties of the above compounds (1)-(6) and (C1)-(C6) were subsequently evaluated as follows. The compounds were solubilized at a concentration of 5 mg in 50 ml THF. Absorption in the UV-visible range of the solution (optical path 1 cm) before and after exposure to a 365 nm UV source was measured. Tint and intensity developed by placing the solutions under sunlight or under a solar simulator were observed. The properties of the compounds are provided in TABLE I below. In this table, $\lambda_1$ denotes the shortest wavelength of the absorption band on the visible spectrum of the solution of the compound after exposure to UV radiation; $\lambda_2$ denotes the longest wavelength of the absorption band on the visible spectrum of the solution of the compound after exposure to UV radiation; and $T_{1/2}$ denotes the discoloration time corresponding to 50% reduction of absorption at $\lambda_2$ at 21° C.

Observation of the solutions in the presence of solar or UV radiation indicated that the compounds of the present invention have slightly higher $\lambda_2$ than their analogous compounds having alkoxy in lieu of the carbamate or urea functions. It can be seen from TABLE I that, $\lambda_2$ of compound (1) is +5 nm higher than that of (C2); $\lambda_2$ of compound (2) is +6 nm higher than that of (C4); $\lambda_2$ of compound (5) is +11 nm higher than that of (C2); and $\lambda_2$ of compound (6) is +12 nm higher than that of (C4). Comparing compounds (4) and (C6), $\lambda_2$ and $\lambda_2$ of compound (4) are +8 nm and +2 nm higher, respectively. These values are small when compared to the gain observed for analogous compound (C1) having morpholino over (C2), which is +33 nm. Compared to compounds (C3) and (C5) having acetamidos, the compounds (1) and (2) of the present invention have similar absorption band (compounds (1) and (C3) have the same $\lambda_2$; $\lambda_2$ of compound (2) is +2 nm higher than that of (C5); $\lambda_2$ of compound (5) is +6 nm higher than that of (C3); and $\lambda_2$ of compound (6) is +8 nm higher than that of compound (C5)). However, unexpectedly, the $T_{1/2}$ data clearly show that compounds (1) and (2) of the present invention are much more rapid in terms of discoloration than (C3) and (C5), and their discoloration kinetics are much closer to those analogous compounds having alkoxy ((C2) and (C4)). Compounds (5) and (6) having urea functions also show more rapid discoloration than compounds (C2) and (C4) having acetamidos, respectively.

TABLE I

| Compound | Structure | $\lambda_1$ (nm) | $\lambda_2$ (nm) | $T_{1/2}$ (s) |
|---|---|---|---|---|
| (1) | 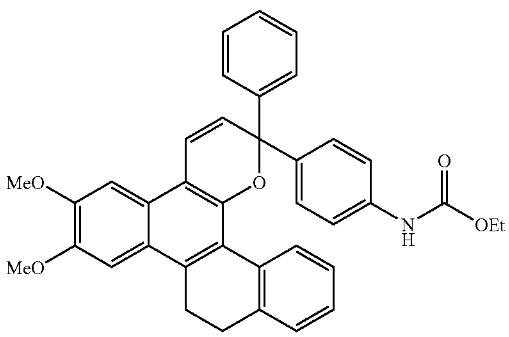 | — | 446 | 36 |
| (2) | 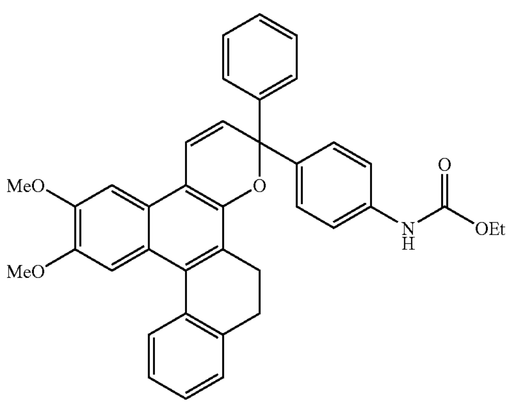 | — | 452 | 34 |
| (3) | 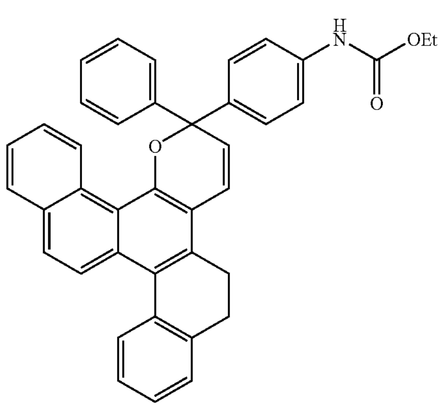 | 450 | 547 | 27 |

TABLE I-continued

| Compound | Structure | λ₁ (nm) | λ₂ (nm) | T₁/₂ (s) |
|---|---|---|---|---|
| (4) | 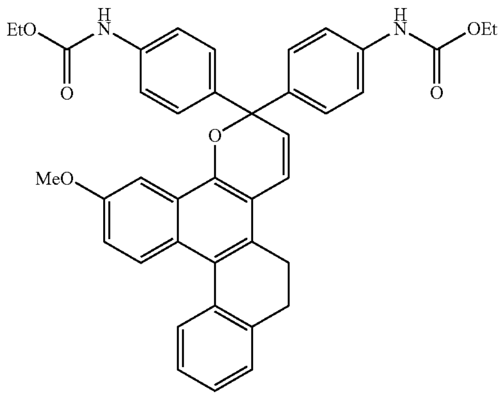 | 443 | 560 | 42 |
| (5) | 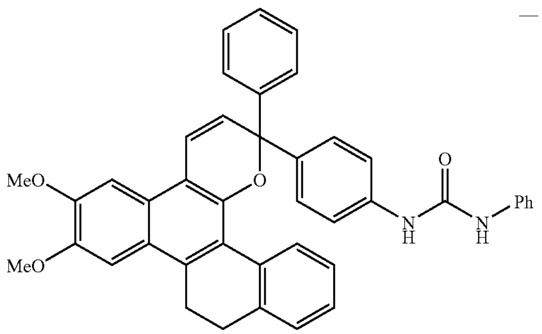 | — | 452 | 36 |
| (6) | 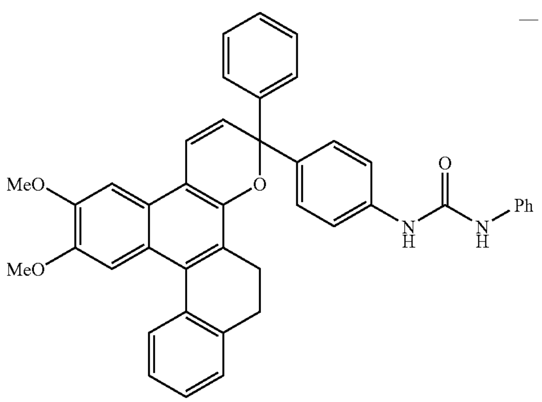 | — | 458 | 29 |
| (C1) | 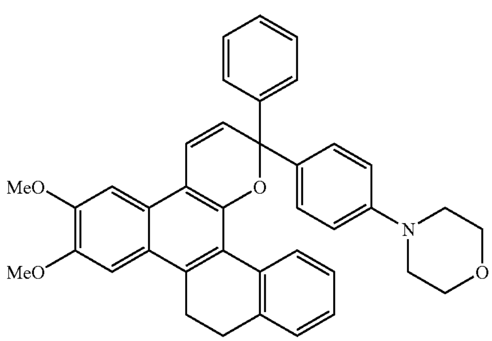 | — | 474 | 20 |

TABLE I-continued

| Compound | Structure | λ₁ (nm) | λ₂ (nm) | T₁/₂ (s) |
|---|---|---|---|---|
| (C2) | 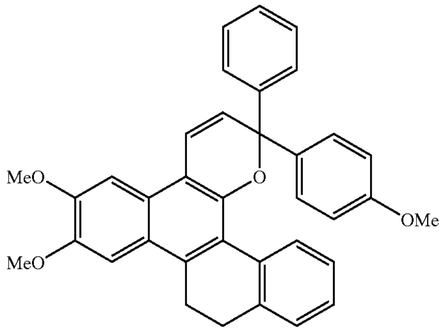 | — | 441 | 30 |
| (C3) | 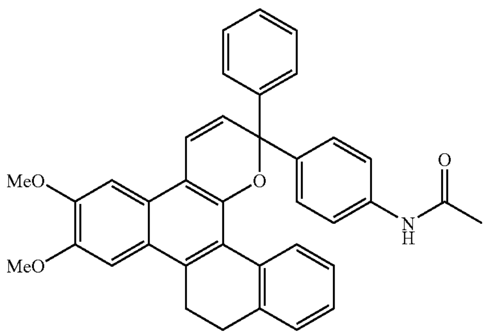 | — | 446 | 45 |
| (C4) | 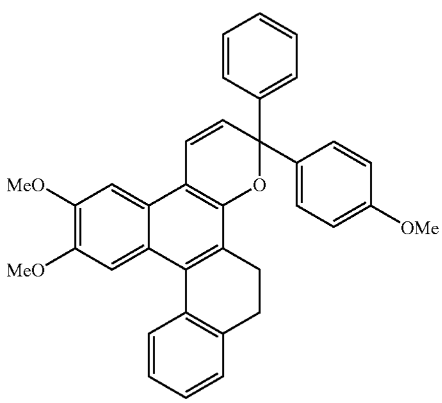 | — | 446 | 23 |
| (C5) | 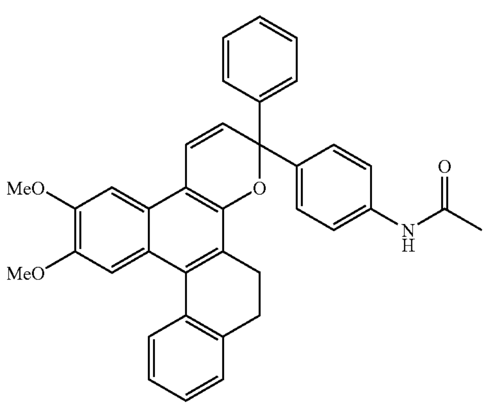 | — | 450 | 42 |

TABLE I-continued

| Compound | Structure | $\lambda_1$ (nm) | $\lambda_2$ (nm) | $T_{1/2}$ (s) |
|---|---|---|---|---|
| (C6) | 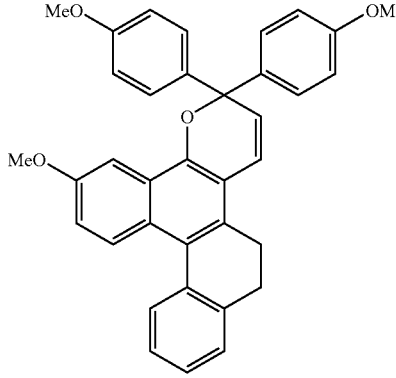 | 435 | 558 | 30 |

The invention claimed is:

1. A compound having the following formula (I)

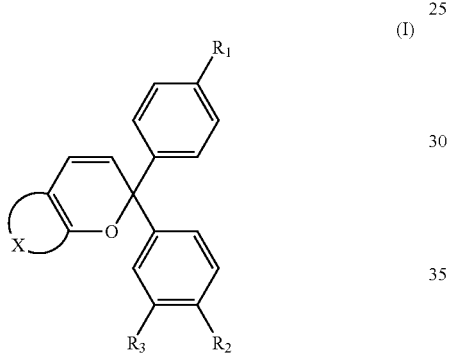

wherein:
(1) $R_1$ represents a group

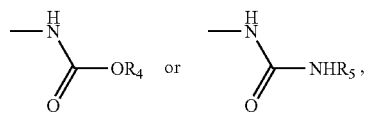

wherein $R_4$ and $R_5$ represent linear or branched alkyl group having 1 to 12 carbon atoms, a benzyl, naplithyl or phenyl group optionally substituted by at least one linear or branched alkyl group having 1 to 6 carbon atoms;

(2) $R_2$ and $R_3$ are defined as follows:
  (A) $R_2$ represents one of the following groups:
    (A1) a hydrogen;
    (A2) a linear or branched alkyl group having 1 to 12 carbon atoms, advantageously 1 to 6 carbon atoms;
    (A3) a cycloalkyl group having 3 to 12 carbon atoms;
    (A4) a phenyl or benzyl group, optionally substituted;
    (A5) a linear or branched alkoxy group having 1 to 12 carbon atoms, advantageously 1 to 6 carbon atoms; and
  (A6) a group

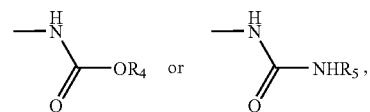

wherein $R_4$ and $R_5$ have the same meaning as defined supra for $R_1$;

(B) $R_3$ represents one of the following groups:
  (B1) a hydrogen;
  (B2) a linear or branched alkyl group having 1 to 12 carbon atoms, advantageously 1 to 6 carbon atoms;
  (B3) a cycloalkyl group having 3 to 12 carbon atoms;
  (B4) a phenyl or benzyl group, optionally substituted; and
  (B5) a linear or branched alkoxy group having 1 to 12 carbon atoms, advantageously 1 to 6 carbon atoms; or (C) the $R_2$ and $R_3$, groups, taken together, form an aromatic or non-aromatic cyclic group having one ring or two annelated rings which can comprise at least one heteroatom selected from the group consisting of: oxygen, sulfur and nitrogen; the aromatic or non-aromatic rings being independently 5 to 7-membered; and (3) the group

is a benzo, naphtho or phenanthro group optionally substituted or annelated with other aromatic or non-aromatic rings.

2. A compound in accordance with claim 1, characterized in that it has one of the following formulae ($I_a$), ($I_b$), ($I_c$) and ($I_d$):

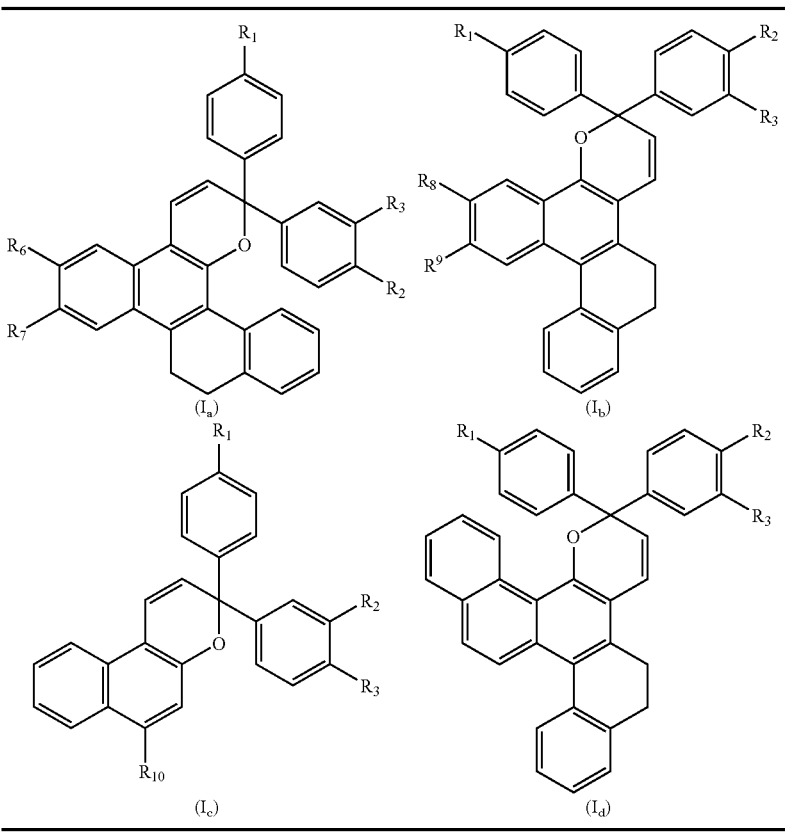

wherein
(a) $R_1$, $R_2$ and $R_3$ have the same definition as given supra in claim 1 in relation to formula (I);
(b) $R_6$ represents:
 (b1) a hydroxy;
 (b2) a linear or branched alkyl comprising 1 to 6 carbon atoms;
 (b3) a linear or branched alkoxy group comprising 1 to 6 carbon atoms;
 (b4) a

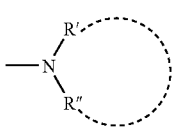

group, where R' and R", identical or different, independently represent a linear or branched alkyl group comprising 1 to 6 carbon atoms, a phenyl group optionally substituted with at least one linear or branched alkyl group comprising 1 to 6 carbon atoms, or together wit the nitrogen atom to which they are bound represent a 5- to 7-membered ring which can comprise at least one other heteroatom selected from oxygen, sulfur and nitrogen, said nitrogen being optionally substituted with an R'" group, which is a linear or branched alkyl group comprising 1 to 6 carbon atoms;

(c) $R_7$ represents:
 (c1) a halogen, and notably fluorine, chlorine or bromine;
 (c2) a hydroxy;
 (c3) a linear or branched alkyl group comprising 1 to 12 carbon atoms (advantageously 1 to 6 carbon atoms);
 (c4) a cycloalkyl having 1-12 carbon atoms;
 (c5) a linear or branched alkoxy group comprising 1 to 12 carbon atoms (advantageously 1 to 6 carbon atoms),
 (c6) a haloalkyl, halocycloalkyl, or haloalkcoxy group corresponding to the alkyl, cycloalkyl, alkoxy groups of (c3), (c4) and (c5) above, respectively, which are substituted with at least one halogen atom, notably selected from fluorine, chlorine and bromine,
 (c7) an aryl or heteroaryl group comprising in its basic structure 6 to 24 carbon atoms or 4 to 24 carbon atoms, or 4 to 24 carbon atoms and at least one heteroatom selected from sulfur, oxygen and nitrogen; said basic structure being optionally substituted with at least one substituent selected from the list given below:
  (c7.1) a halogen, and notably fluorine, chlorine and bromine;
  (c7.2) a hydroxy;
  (c7.3) a linear or branched alkyl group comprising 1 to 12 carbon atoms, advantageously 1-6 carbon atoms;

(c7.4) a linear or branched alkoxy group comprising 1 to 12 carbon atoms, advantageously 1-6 carbon atoms;
(c7.5) a cycloalkyl group comprising 3 to 12 carbon atoms,
(c7.6) a haloalkyl, haloalkoxy or halocycloalkyl group corresponding respectively to the alkyl, alkoxy and cycloalkyl defined in (c7.3), (c7.4) and (c7.5), supra, which are substituted with at least one halogen atom, and notably a fluorine atom;
(c7.7) a phenoxy or naphthoxy group optionally substituted with at least one linear or branched alkyl or alkoxy group comprising 1 to 12 carbon atoms;
(c7.8) a linear or branched alkenyl group comprising 2 to 12 carbon atoms, and notably a vinyl group or an allyl group;
(c7.9) an —$NH_a$ group;
(c7.10) an —NHR group, with R representing a linear or branched alkyl group comprising 1 to 6 carbon atoms, or a phenyl group optionally substituted with at least one linear or branched alkyl group comprising 1 to 6 carbon atoms;
(c7.11) a

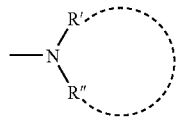

group, where R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R'" group, which is a linear or branched alkyl group comprising 1 to 6 carbon atoms;
(c.7.12) a methacryloyl group or an acryloyl group;
(c8) an aralkyl or heteroaralkyl group, the alkyl group, which is linear or branched, comprises 1 to 4 carbon atoms, and the aryl and heteroaryl groups have the same definition as those given supra in (c7) in this claim;
(c9) a phenoxy or naphthoxy group optionally substituted with at least one linear or branched alkyl or alkoxy group comprising 1 to 12 carbon atoms,
(c10) an amine, amide, carbamate or urea group: —$NH_2$, —NHCOR, —NHCOR, —NR'COR, —NHCOOR, —NHCONHR, —$CONH_2$, —CONHR,

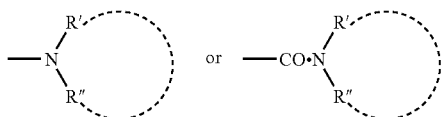

wherein
R represents a linear or branched alkyl group comprising 1 to 6 carbon atoms, or a phenyl group optionally substituted with at least one linear or branched alkyl group comprising 1 to 6 carbon atoms;
R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R'" group, which is a linear or branched alkyl group comprising 1 to 6 carbon atoms;
(c11) an —$OCOR_{11}$ or —$OCOOR_{11}$ group, $R_{11}$ representing a linear or branched alkyl group comprising 1 to 6 carbon atoms, or a cycloalkyl group comprising 3 to 6 atoms, or a phenyl group, optionally substituted with at least one of the substituents listed above in (c7.1) to (c7.12) for the aryl and heteroaryl groups defined in (c7);

or $R_6$ and $R_7$, taken together, form an aromatic or non-aromatic cyclic group having one ring or two annelated rings, which can comprise at least one heteroatom selected from the group consisting of: oxygen, sulfur and nitrogen; wherein the aromatic or non-aromatic rings are independently 5 to 7-membered and optionally comprises at least one substituent $R_3$ as defined in claim 1 supra in relation to formula (I);
(d) $R_8$ and $R_9$, identical or different, independently represent:
(d1) a halogen, and notably fluorine, chlorine or bromine;
(d2) a hydroxy;
(d3) a linear or branched alkyl group comprising 1 to 12 carbon atoms (advantageously 1 to 6 carbon atoms);
(d4) a cycloalkyl group comprising 1-12 carbon atoms;
(d5) a linear or branched alkoxy group comprising 1 to 12 carbon atoms (advantageously 1 to 6 carbon atoms),
(d6) a haloalkyl, halocycloalkyl, or haloalkoxy group corresponding to the alkyl, cycloalkyl, alkoxy groups in (d3), (d4) and (d5), respectively, which are substituted with at least one halogen atom, notably selected from fluorine, chlorine and bromine,
(d7) an aryl or heteroaryl group having the same definition as given above for $R_7$ in (c7), supra;
(d8) an aralkyl or heteroaralkyl group, wherein the alkyl group, linear or branched, comprises 1 to 4 carbon atoms, and the aryl and heteroaryl groups have the same definition as those given supra in (c7);
(d9) a phenoxy or naphthoxy group optionally substituted with at least one linear or branched alkyl or alkoxy group comprising 1 to 12 carbon atoms,
(d10) an amine, amide, carbamate or urea group: —$NH_2$, —NHR, —NHCOR, —NR'COR, —NHCOOR, —NHCONHR, —$CONH_2$, —CONHR,

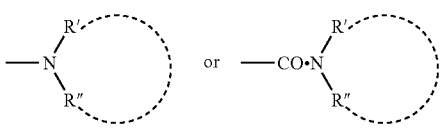

wherein

R represents a linear or branched alkyl group comprising 1 to 6 carbon atoms, or a phenyl group optionally substituted with at least one linear or branched alkyl group comprising 1 to 6 carbon atoms;

R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms;

(d11) an —OCOR$_{11}$ or OCOOR$_{11}$ group, R$_{11}$ representing a linear or branched alkyl group comprising 1 to 6 carbon atoms, or a cycloalkyl group comprising 3 to 6 atoms, or a phenyl group, optionally substituted with at least one of the substituents listed above from (c7.1) to (c7.12) for the aryl and heteroaryl groups defined in (c7) of this claim;

or

R$_8$ and R$_9$, taken together, form an aromatic or non-aromatic cyclic group having one or two annelated rings which can comprise at least one heteroatom selected from the group consisting of oxygen, sulfur and nitrogen; wherein said rings, being 5-7 membered, optionally comprises at least one substituent selected from those listed from (c7.1) to (c7.12) for the aryl and heteroaryl groups defined in (c7) of this claim;

(e) R$_{10}$ represents a

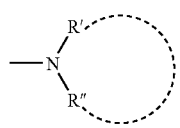

group, where R' and R", identical or different, independently represent a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms.

3. A compound according to claim 1, having the following formula (I1):

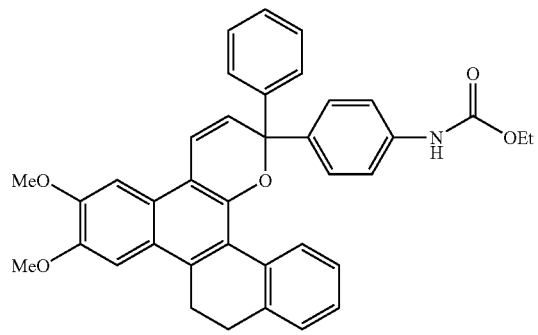

4. A compound according to claim 1 having the following formula (I2):

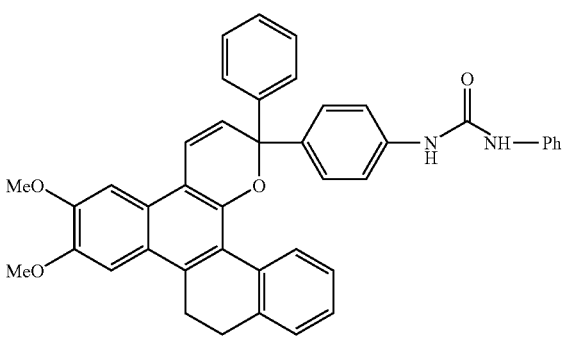

5. A compound according to claim 1 having the following formula (I3):

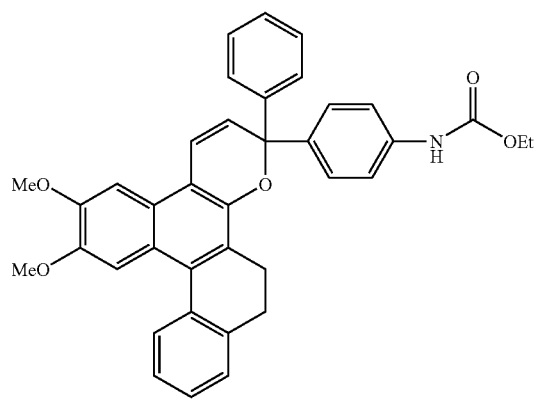

6. A compound according to claim 1 having the following formula (I4):

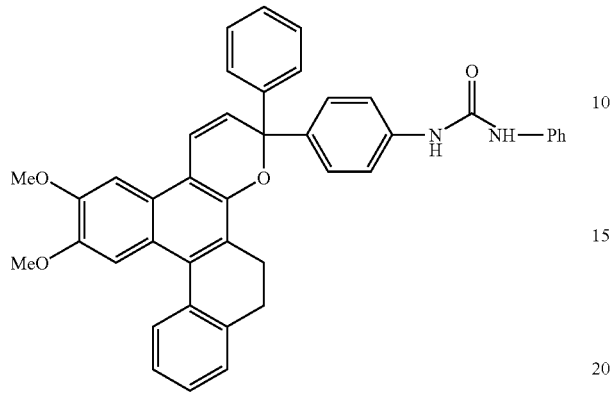

7. A compound according to claim 1 having the following formula (I5):

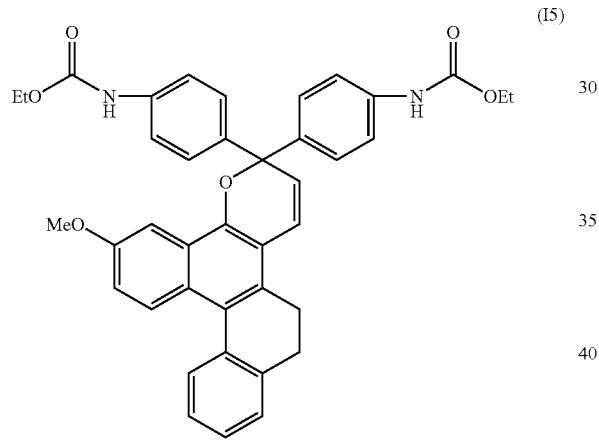

8. A compound according to claim 1 having the following formula (I6):

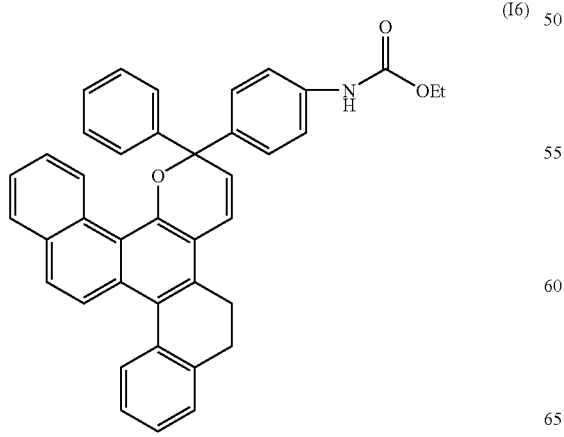

9. A photochromic composition comprising in part at least one compound having the following formula (I):

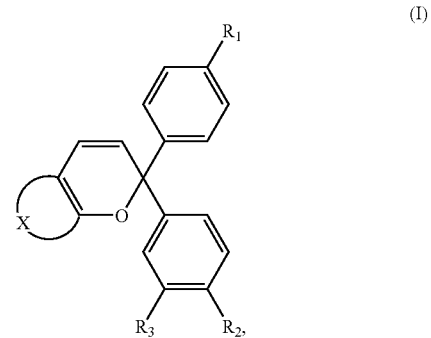

wherein:
(1) $R_1$ represents a group

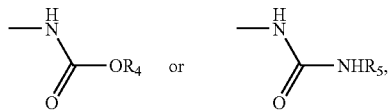

wherein $R_4$ and $R_5$ represent linear or branched alkyl group having 1 to 12 carbon atoms, a benzyl, naphthyl or phenyl group optionally substituted by at least one linear or branched alkyl group having 1 to 6 carbon atoms:

(2) $R_2$ and $R_3$ are defined as follows:
(A) $R_2$ represents one of the following groups:
(A1) a hydrogen;
(A2) a linear or branched alkyl group having to 12 carbon atoms, advantageously 1 to 6 carbon atoms;
(A3) a cycloalkyl group having 3 to 12 carbon atoms;
(A4) a phenyl or benzyl group, optionally substituted;
(A5) a linear or branched alkoxy group having 1 to 12 carbon atoms, advantageously 1 to 6 carbon atoms; and
(A6) a group

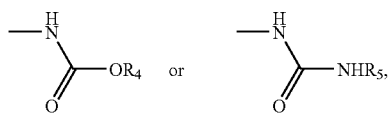

wherein $R_4$ and $R_5$ have the same meaning as defined supra for $R_1$;

(B) $R_3$ represents one of the following groups:
(B1) a hydrogen;
(B2) a linear or branched alkyl group having 1 to 12 carbon atoms, advantageously 1 to 6 carbon atoms;
(B3) a cycloalkyl group having 3 to 12 carbon atoms;
(B4) a phenyl or benzyl group, optionally substituted; and (B5) a linear or branched alkoxy group having 1 to 12 carbon atoms. advantageously 1 to 6 carbon atoms;

or (C) the $R_2$ and $R_3$ groups, taken together, form an aromatic or non-aromatic cyclic group having one ring or two annelated rings which can comprise at least one heteroatom selected from the group consisting of: oxygen, sulfur and nitrogen; the aromatic or non-aromatic rings being independently 5 to 7-membered; and (3) the group

is a benzo, naphtho or phenanthro group optionally substituted or annelated with other aromatic or non-aromatic rings.

10. A photochromic composition according to claim 9, wherein the at least one compound has one of the following formulae $(I_a)$, $(I_b)$, $(I_c)$ and $(I_d)$:

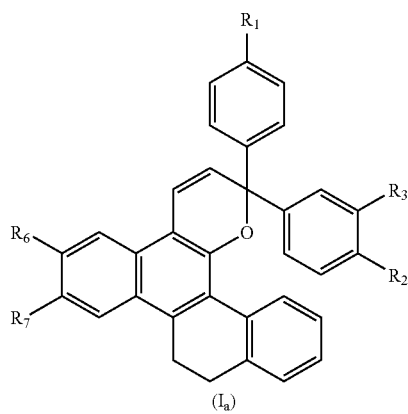

(I$_a$)

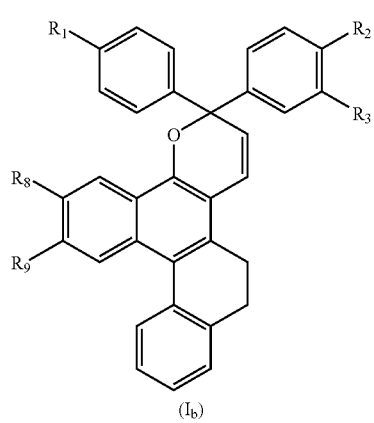

(I$_b$)

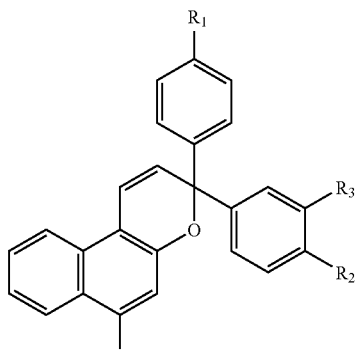

(I$_c$)

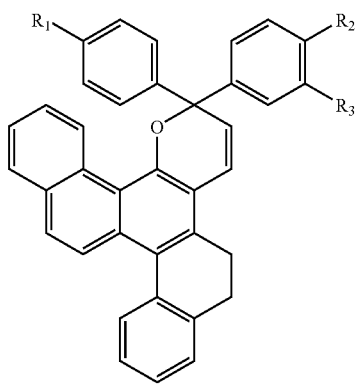

(I$_d$)

wherein (a) $R_1$, $R_2$ and $R_3$ have the same definition as given supra in claim 9s in relation to formula (I);

(b) $R_6$ represents:

(b1) a hydroxy;

(b2) a linear or branched alkyl comprising 1 to 6 carbon atoms;

(b3) a linear or branched alkoxy group comprising 1 to 6 carbon atoms;

(b4) a

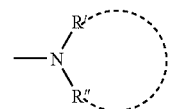

group, where R' and R", identical or different independently represent a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms;
(c) $R_7$ represents:
(c1) a halogen, and notably fluorine, chlorine or bromine;
(c2) a hydroxy;
(c3) a linear or branched alkyl group comprising 1 to 12 carbon atoms (advantageously 1 to 6 carbon atoms):
(c4) a cycloalkyl having 1-12 carbon atoms;
(c5) a linear or branched alkoxy group comprising 1 to 12 carbon atoms (advantageously 1 to 6 carbon atoms),
(c6) a haloalkyl, halocycloalkcyl, or haloalkoxy group corresponding to the alkyl, cycloalkyl, alkoxy groups of (c3), (c4) and (c5) above, respectively, which are substituted with at least one halogen atom, notably selected from fluorine, chlorine and bromine,
(c7) an aryl or heteroaryl group comprising in its basic structure 6 to 24 carbon atoms or 4 to 24 carbon atoms, or 4 to 24 carbon atoms and at least one heteroatom selected from sulfur, oxygen and nitrogen; said basic structure being optionally substituted with at least one substituent selected from the list given below:
(c7.1) a halogen, and notably fluorine, chlorine and bromine;
(c7.2) a hydroxy;
(c7.3) a linear or branched alkyl group comprising 1 to 12 carbon atoms, advantageously 1-6 carbon atoms;
(c7.4) a linear or branched alkoxy group comprising 1 to 12 carbon atoms, advantageously 1-6 carbon atoms;
(c7.5) a cycloalkyl group comprising 3 to 12 carbon atoms,
(c7.6) a haloalkyl, haloalkoxy or halocycloalkyl group corresponding respectively to the alkyl, alkoxy and cycloalkyl defined in (c7.3), (c7.4) and (c7.5), supra, which are substituted with at least one halogen atom, and notably a fluorine atom;
(c7.7) a phenoxy or naphthoxy group optionally substituted with at least one linear or branched alkyl or alkoxy group comprising 1 to 12 carbon atoms;
(c7.8) a linear or branched alkenyl group comprising 2 to 12 carbon atoms, and notably a vinyl group or an allyl group;
(c7.9) an —$NH_2$ group;
(c7.10) an —NHR group, with R representing a linear or branched alkyl group comprising 1 to 6 carbon atoms, or a phenyl group optionally substituted with at least one linear or branched alkyl group comprising 1 to 6 carbon atoms;
(c7.11) a

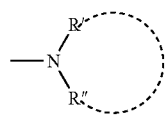

group, where R' and R'', identical or different represent independently a linear or branched alkyl group comprising 1 to 6 carbon atoms, a phenyl group optionally substituted with at least one linear or branched alkyl group comprising 1 to 6 carbon atoms or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms;
(c7.12) a methacryloyl group or an acryloyl group;
(c8) an aralkyl or heteroaralkyl group, the alkyl group, which is linear or branched, comprises 1 to 4 carbon atoms, and the aryl and heteroaryl groups have the same definition as those given supra in (c7) in this claim;
(c9) a phenoxy or naphthoxy group optionally substituted with at least one linear or branched alkyl or alkoxy group comprising 1 to 12 carbon atoms,
(c10) an amine, amide, carbamate or urea group: —$N_2$, —NHR, —NHCOR, —NR'COR. —NHCOOR, —NHCONHR, —CONH, —CONHR,

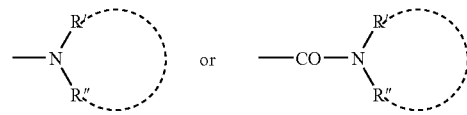

wherein
R represents a liner or branched alkyl group comprising 1 to 6 carbon atoms, or a phenyl group optionally substituted with at least one linear or branched alkyl group comprising 1 to 6 carbon atoms;
R' and R'', identical or different represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms;
(c11) an —$OCOR_{11}$ or $OCOOR_{11}$ group $R_{11}$ representing a linear or branched alkyl group comprising 1 to 6 carbon atoms, or a cycloalkyl group comprising 3 to 6 atoms, or a phenyl group, optionally substituted with at least one of the substituents listed above in (c7.1) to (c7.12) for the aryl and heteroaryl groups defined in (c7);
or
$R_6$ and $R_7$, taken together, form an aromatic or non-aromatic cyclic group having one ring or two annelated rings, which can comprise at least one heteroatom, selected from the group consisting of: oxygen, sulfur and nitrogen; wherein the aromatic or non-aromatic rings are independently 5 to 7-membered and optionally comprises at least one substituent $R_3$ as defined in claim 1 supra in relation to formula (I);

(d) $R_8$ and $R_9$, identical or different, independently represent:
- (d1) a halogen, and notably fluorine, chlorine or bromine;
- (d2) a hydroxy;
- (d3) a linear or branched alkyl group comprising 1 to 12 carbon atoms (advantageously 1 to 6 carbon atoms);
- (d4) a cycloalkyl group comprising 1-12 carbon atoms;
- (d5) a linear or branched alkoxy group comprising 1 to 12 carbon atoms (advantageously 1 to 6 carbon atoms),
- (d6) a haloalkyl, halocycloalkyl, or haloalkoxy group corresponding to the alkyl, cycloalkyl, alkoxy groups in (d3), (d4) and (d5), respectively, which are substituted with at least one halogen atom, notably selected from fluorine, chlorine and bromine,
- (d7) an aryl or heteroaryl group having the same definition as given above for $R_7$ in (c7), supra;
- (d8) an aralkyl or heteroaralkyl group, wherein the alkyl group, linear or branched, comprises 1 to 4 carbon atoms, and the aryl and heteroaryl groups have the same definition as those given supra in (c7);
- (d9) a phenoxy or naphthoxy group optionally substituted with at least one linear or branched alkyl or alkoxy group comprising 1 to 12 carbon atoms,
- (d10) an amine, amide, carbamate or urea group: —$NH_2$, —NHR, —NHCOR, —NR'COR, —NHCOOR, —NHCONHR, —$CONH_2$, —CONHR,

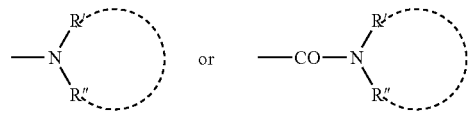

wherein
R represents a linear or branched alkyl group comprising 1 to 6 carbon atoms, or a phenyl group optionally substituted with at least one linear or branched alkyl group comprising 1 to 6 carbon atoms;
R' and R", identical or different, represent independently a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms;
- (d11) an —$OCOR_{11}$ or $OCOOR_{11}$ group, $R_{11}$ representing a liner or branched alkyl group comprising 1 to 6 carbon atoms, or a cycloalkyl group comprising 3 to 6 atoms, or a phenyl group, optionally substituted with at least one of the substituents listed above from (c7.1) to (c7.12) for the aryl and heteroaryl groups defined in (c7) of this claim;

or $R_8$ and $R_9$, taken together, form an aromatic or non-aromatic cyclic group having one or two annelated rings which can comprise at least one heteroatom selected from the group consisting of oxygen, sulfur and nitrogen; wherein said rings, being 5-7 membered, optionally comprises at least one substituent selected from those listed from (c7.1) to (c7.12) for the aryl and heteroaryl groups defined in (c7) of this claim:

(e) $R_{10}$ represents a

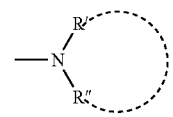

group, where R' and R", identical or different, independently represent a linear or branched alkyl group comprising 1 to 6 carbon atoms, a phenyl group optionally substituted with at least one linear or branched alkyl group comprising 1 to 6 carbon atoms, or together with the nitrogen atom to which they are bound represent a 5- to 7-membered ring which can comprise at least one other heteroatom selected from oxygen, sulfur and nitrogen, said nitrogen being optionally substituted with an R''' group, which is a linear or branched alkyl group comprising 1 to 6 carbon atoms.

11. A photochromic composition according to claim 9, wherein the at least one compound is selected from the following compounds (I1)-(I6):

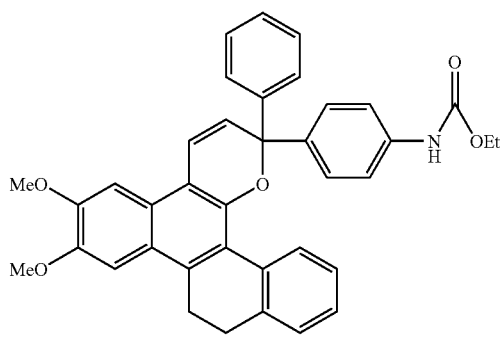

(I1)

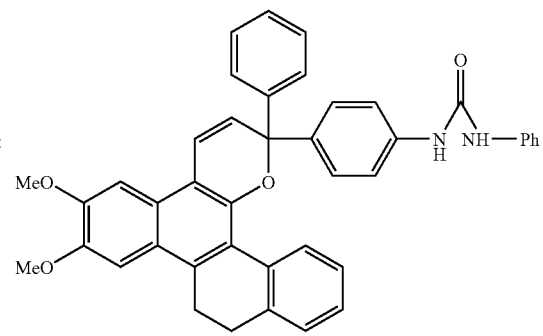

(I4)

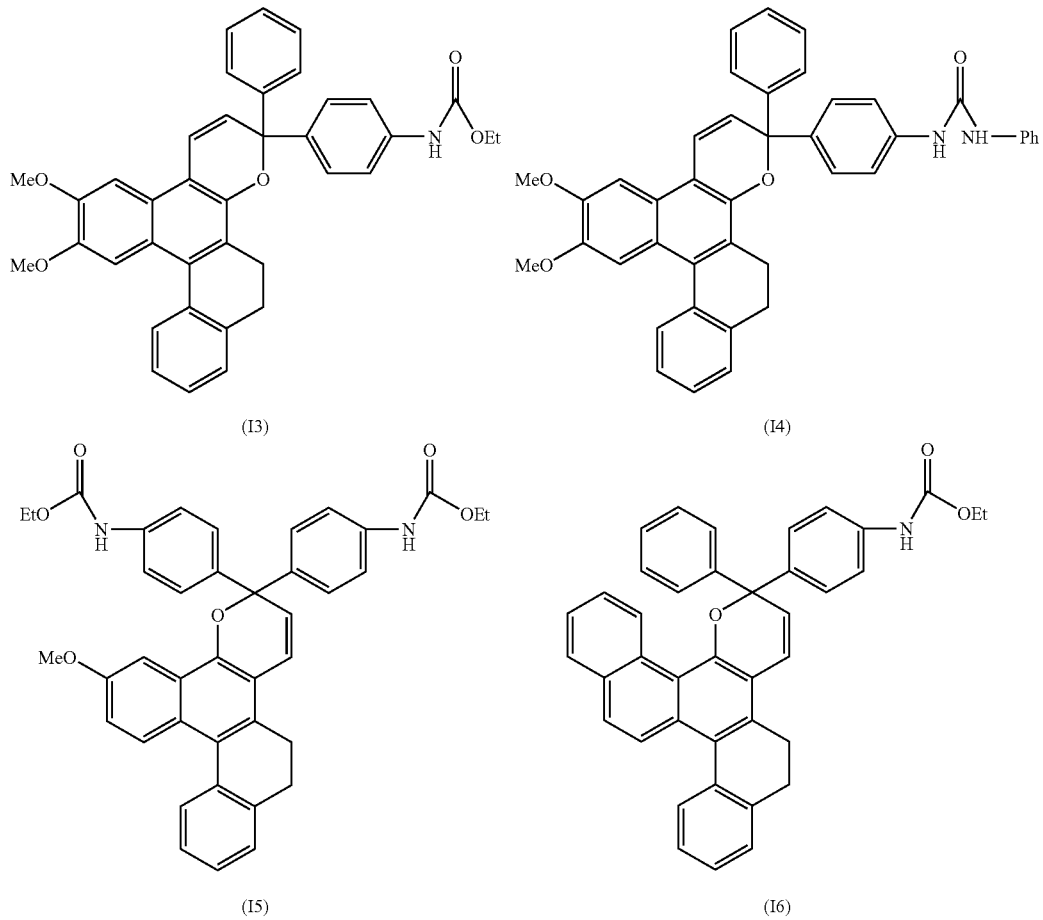

(I3) (I4) (I5) (I6)

12. A photochromic composition according to claim 9, characterized in that it further comprises at least one other type of photochromic compound and/or at least one non-photochromic colorant.

13. A photochromic composition according to claim 9, characterized in that it comprises a linear or reticulated (co)polymer obtained by polymerization and/or reticulation and/or grafting of at least one compound defined in claim 9.

14. A photochromic composition according to claim 12, characterized in that it comprises a linear or reticulated (co)polymer obtained by polymerization and/or reticulation and/or grafting of at least one compound defined in claim 9.

15. A photochromic composition according to claim 9, characterized in that it comprises at least one (co)polymer constituted by or selected from the following:

(1) mono-, di-, tri- or tetraacrylate or mono-, di-, tri- or tetramethacrylate of alkyl, cycloalkyl, (poly or oligo) ethylene glycol, aryl or arylalkyl, optionally halogenated or comprising at least one group selected from: ether, ester, carbonate, carbamate, thiocarbamate, urea, amide and combinations thereof;

(2) polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetatepropionate, and polyvinylbutyral;

(3) difunctional monomers corresponding to the following formula (Z):

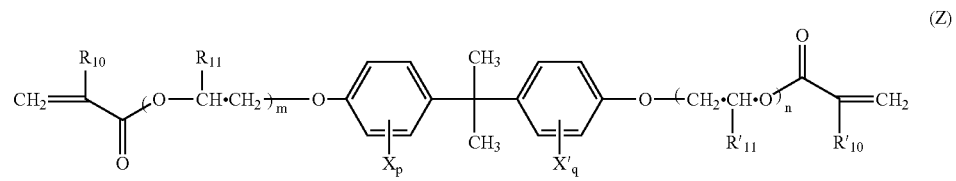

(Z)

wherein
(i) $R_{10}$, $R'_{10}$, $R_{11}$ and $R'_{11}$, identical or different, independently represent a hydrogen or a methyl group;
(ii) m and n are independently integers between 0 and 4 inclusive, and are advantageously independently equal to 1 or 2;
(iii) X and X', identical or different, are a halogen and preferably represent a chlorine and/or a bromine; and
(iv) p and q are, independently, integers between 0 and 4 inclusive; and
(4) copolymers of at least two types of copolymerizable monomers defined supra in this claim, and preferably those of(meth)acrylic, vinylic, allylic types and their mixtures.

16. An ophthalmic or solar article comprising a compound having the following formula (I):

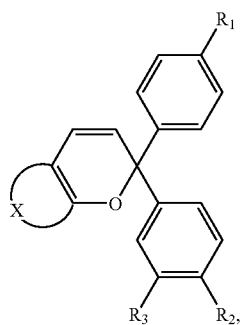

wherein:
(1) $R_1$ represents a group

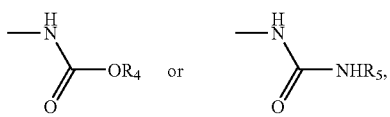

wherein $R_4$ and $R_5$ represent linear or branched alkyl group having 1 to 12 carbon atoms, a benzyl, naphthyl or phenyl group optionally substituted by at least one linear or branched alkyl group having 1 to 6 carbon atoms:
(2) $R_2$ and $R_5$ are defined as follows:
(A) $R_2$ represents one of the following groups:
(A1) a hydrogen;
(A2) a linear or branched alkyl group having 1 to 12 carbon atoms, advantageously 1 to 6 carbon atoms;
(A3) a cycloalkyl group having 3 to 12 carbon atoms;
(A4) a phenyl or benzyl group, optionally substituted;
(A5) a linear or branched alkoxy group having 1 to 12 carbon atoms, advantageously 1 to 6 carbon atoms; and (A6) a group

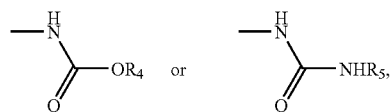

wherein $R_4$ and $R_5$ have the same meaning as defined supra for $R_1$;
(B) $R_3$ represents one of the following groups:
(B1) a hydrogen;
(B2) a linear or branched alkyl group having 1 to 12 carbon atoms, advantageously 1 to 6 carbon atoms;
(B3) a cycloalkyl group having 3 to 12 carbon atoms;
(B4) a phenyl or benzyl group, optionally substituted; and
(B5) a linear or branched alkoxy group having 1 to 12 carbon atoms, advantageously 1 to 6 carbon atoms;
or
(C) the $R_2$ and $R_3$ groups, taken together, form an aromatic or non-aromatic cyclic group having one ring or two annelated rings which can comprise at least one heteroatom selected from the group consisting of: oxygen, sulfur and nitrogen; the aromatic or non-aromatic rings being independently 5 to 7-membered; and
(3) the group

is a benzo, naphtho or phenanthro group optionally substituted or annelated with other aromatic or non-aromatic rings.

17. An ophthalmic or solar article according to claim 16 comprising a photochromic composition comprising in part at least one compound having the formula (I) defined in claim 16.

18. An article according to claim 16, characterized in that it is a lens, a window pane or an optical device.

19. A process for preparing a compound according to claim 1, characterized in that it comprises either:
(1) the condensation reaction between:
(i) an intermediate compound having the following formula (II):

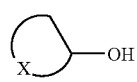

wherein the group

has the same meaning as defined in claim 1 in relation to formula (I); and (ii) a derivative of propargylic alcohol corresponding to the following formula (III):

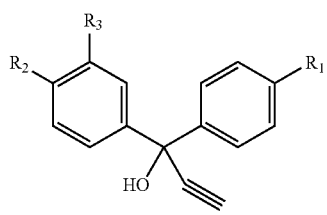

(III)

wherein $R_1$, $R_2$ and $R_3$ have the sane meaning as defined in claim 1 in relation to formula (I);

the condensation between (II) and (III) being advantageously effected in the presence of a catalyst, the catalyst being preferably selected from the group consisting of p-toluenesulfonic acid, dodecylsulfonic acid, camphorsulfonic acid or bromoacetic acid;

or (2) the condensation, reaction between:

the formula (II) compound as defined in (i) supra in this claim, and (iii) an aldehyde derivative corresponding to the following formula (III'):

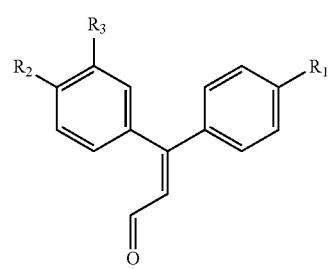

(III')

wherein $R_1$, $R_2$ and $R_3$ have the same meaning as defined in claim 1 in relation to formula (I);

the condensation reaction between (II) and (III') being advantageously effected in the presence of a metal complex, preferably a titanium complex, with titanium tetraethylate being particularly preferred.

* * * * *